US007596703B2

(12) United States Patent
Kohiyama et al.

(10) Patent No.: US 7,596,703 B2
(45) Date of Patent: Sep. 29, 2009

(54) HIDDEN DATA BACKUP AND RETRIEVAL FOR A SECURE DEVICE

(75) Inventors: Tomohisa Kohiyama, Sunnyvale, CA (US); Motoyasu Tsunoda, Kanagawa (JP)

(73) Assignee: Hitachi, Ltd., Tokyo (JP)

( * ) Notice: Subject to any disclaimer, the term of this patent is extended or adjusted under 35 U.S.C. 154(b) by 1237 days.

(21) Appl. No.: 10/393,906

(22) Filed: Mar. 21, 2003

(65) Prior Publication Data

US 2004/0187012 A1  Sep. 23, 2004

(51) Int. Cl.
H04L 9/32  (2006.01)
H04L 9/00  (2006.01)
H04K 1/00  (2006.01)
H04L 9/28  (2006.01)
G06F 17/30  (2006.01)

(52) U.S. Cl. .................. 713/193; 713/165; 713/181; 713/184; 713/185; 380/269; 380/255; 380/28; 726/4; 726/5; 726/27; 707/9; 707/10

(58) Field of Classification Search .................. 713/165, 713/181, 193; 380/269
See application file for complete search history.

(56) References Cited

U.S. PATENT DOCUMENTS

| 4,304,990 | A | * | 12/1981 | Atalla | 380/45 |
| 4,317,957 | A | | 3/1982 | Sendrow | |
| 5,710,817 | A | * | 1/1998 | Sjooquist | 713/159 |
| 5,815,665 | A | | 9/1998 | Teper et al. | |
| 5,841,871 | A | * | 11/1998 | Pinkas | 713/155 |
| 6,018,583 | A | * | 1/2000 | Hawthorne | 713/183 |
| 6,378,075 | B1 | | 4/2002 | Goldstein et al. | |
| 6,678,828 | B1 | * | 1/2004 | Pham et al. | 726/2 |
| 6,732,106 | B2 | * | 5/2004 | Okamoto et al. | 707/100 |
| 6,799,273 | B1 | * | 9/2004 | Oishi et al. | 713/171 |
| 7,082,535 | B1 | * | 7/2006 | Norman et al. | 713/163 |
| 2001/0029581 | A1 | * | 10/2001 | Knauft | 713/193 |
| 2001/0044787 | A1 | | 11/2001 | Shwartz et al. | |
| 2002/0069357 | A1 | * | 6/2002 | Kilkkila | 713/169 |
| 2002/0073066 | A1 | * | 6/2002 | Coutts et al. | 707/1 |
| 2002/0077992 | A1 | | 6/2002 | Tobin | |
| 2002/0112027 | A1 | | 8/2002 | McHugh et al. | |
| 2002/0188849 | A1 | * | 12/2002 | Kwan | 713/176 |
| 2003/0163691 | A1 | * | 8/2003 | Johnson | 713/168 |
| 2004/0123127 | A1 | * | 6/2004 | Teicher et al. | 713/193 |

(Continued)

FOREIGN PATENT DOCUMENTS

JP  08-123758  5/1996

(Continued)

Primary Examiner—Christopher A Revak
Assistant Examiner—Aravind K Moorthy
(74) Attorney, Agent, or Firm—Sughrue Mion, PLLC

(57) ABSTRACT

An agent computer system, acting on behalf of the user, provides the personal information to various wide area network sites for conducting online transactions. A user has a secure device with a built-in device identifier. A backup center has a computer system to be coupled to the secure device during backup of the personal information. The personal information is encrypted with a unique user ID as a key. The user ID is entered by the user. The user ID is irreversibly encrypted to a unique irreversibly encrypted user identifier. The secure device includes data executable to establish a new account, renew an old account, and transmission of the encrypted information along with the unique device identifier and the unique irreversibly encrypted user identifier to the backup center. The unique device identifier and the unique irreversibly encrypted user identifier are used for indexing the storage of the encrypted information.

8 Claims, 14 Drawing Sheets

U.S. PATENT DOCUMENTS

2006/0005237 A1 * 1/2006 Kobata et al. .................. 726/12

FOREIGN PATENT DOCUMENTS

| JP | 11-298639 | 10/1999 |
| JP | 2001-027963 | 1/2001 |
| JP | 2002-149497 | 5/2002 |
| JP | 2002-314706 | 10/2002 |
| WO | WO 0011537 A1 * | 3/2000 |
| WO | WO 00/42540 | 7/2000 |

* cited by examiner

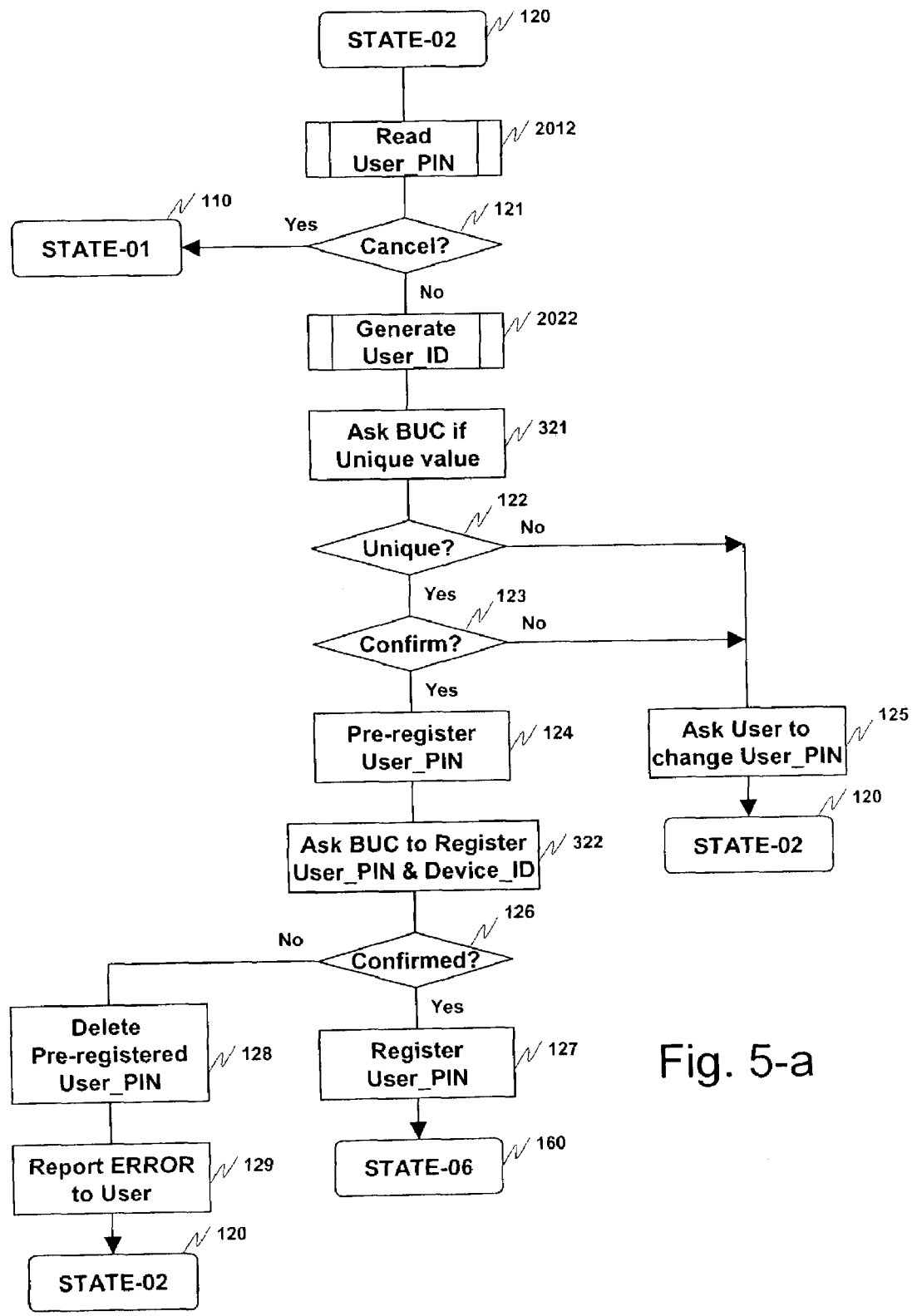
Fig. 5-a

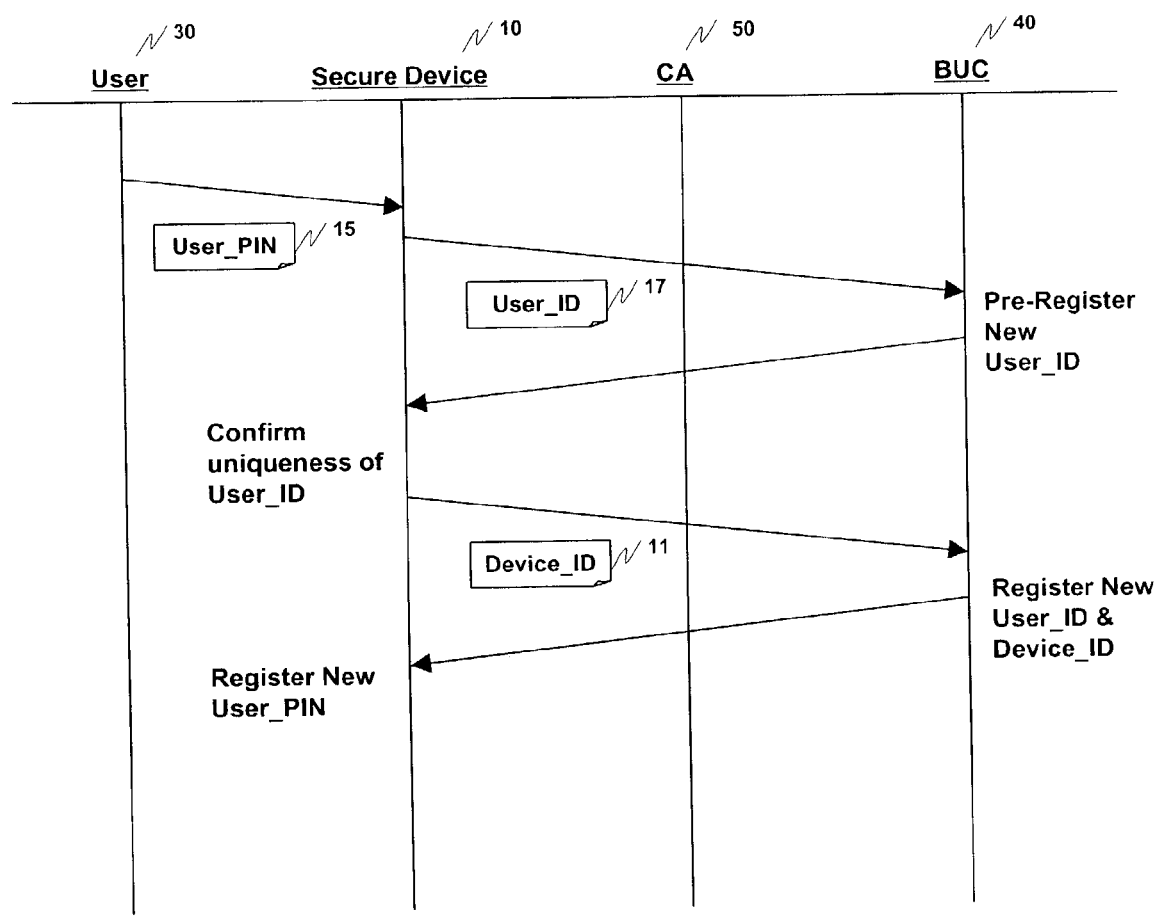
Fig. 5-b

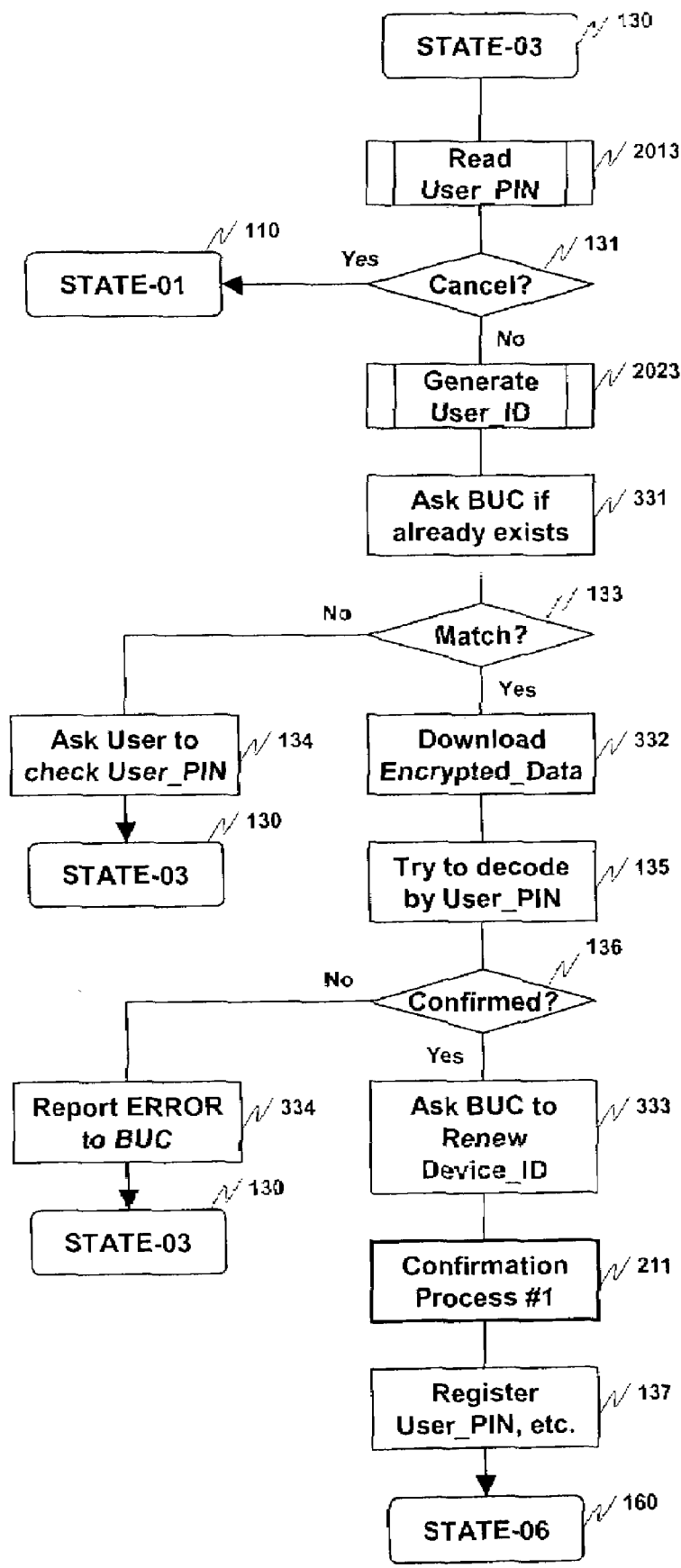
Fig. 6-a

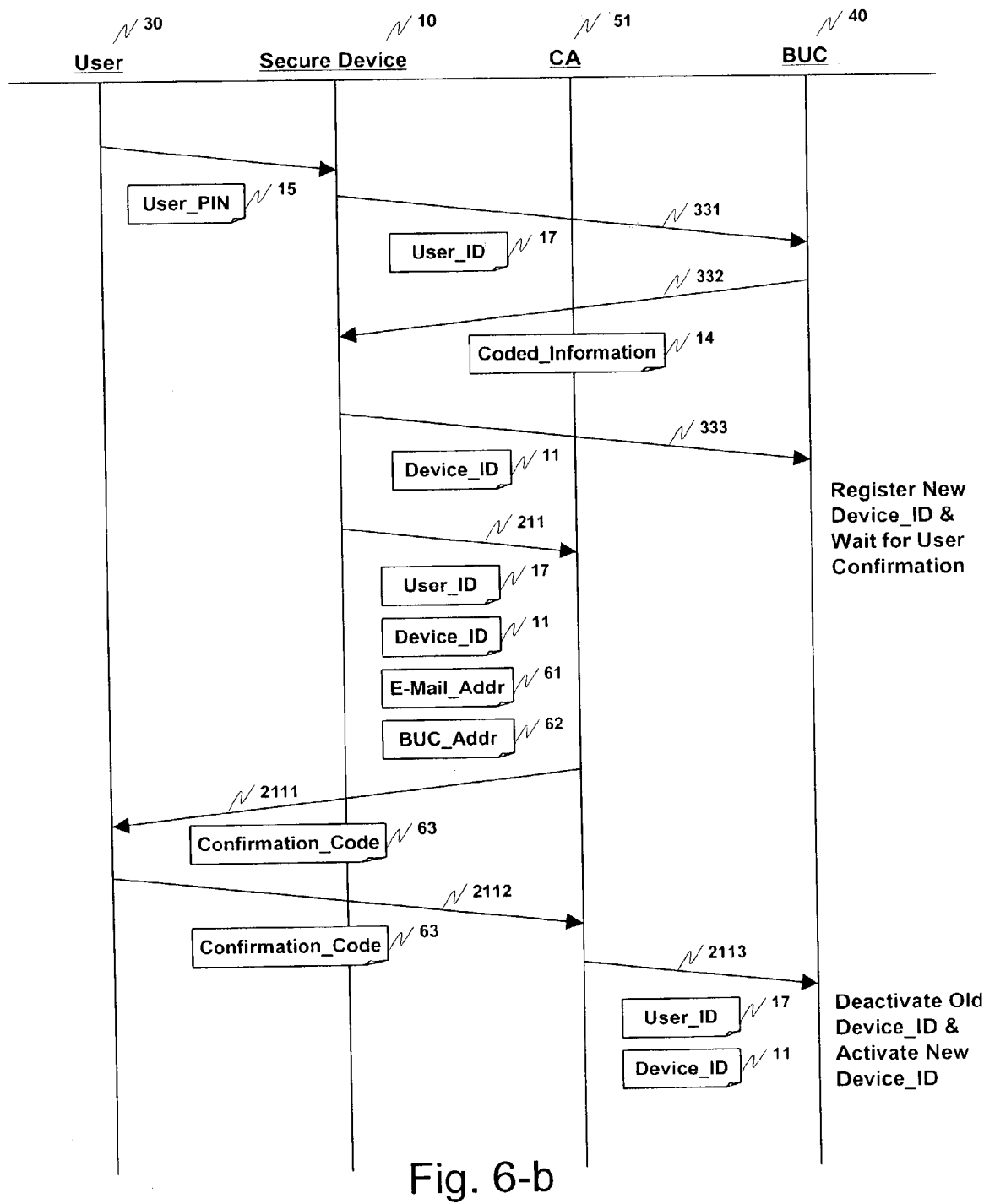
Fig. 6-b

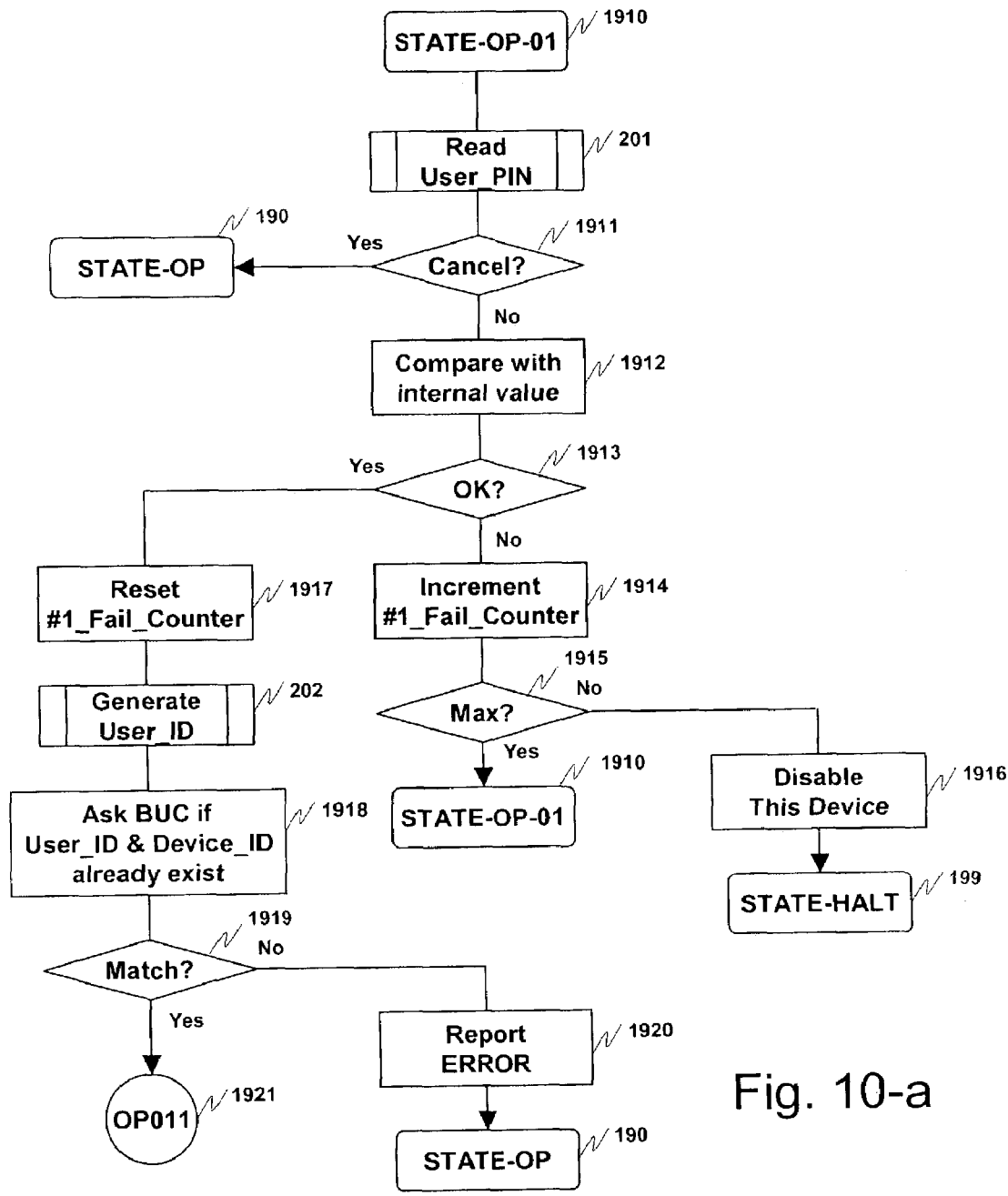
Fig. 10-a

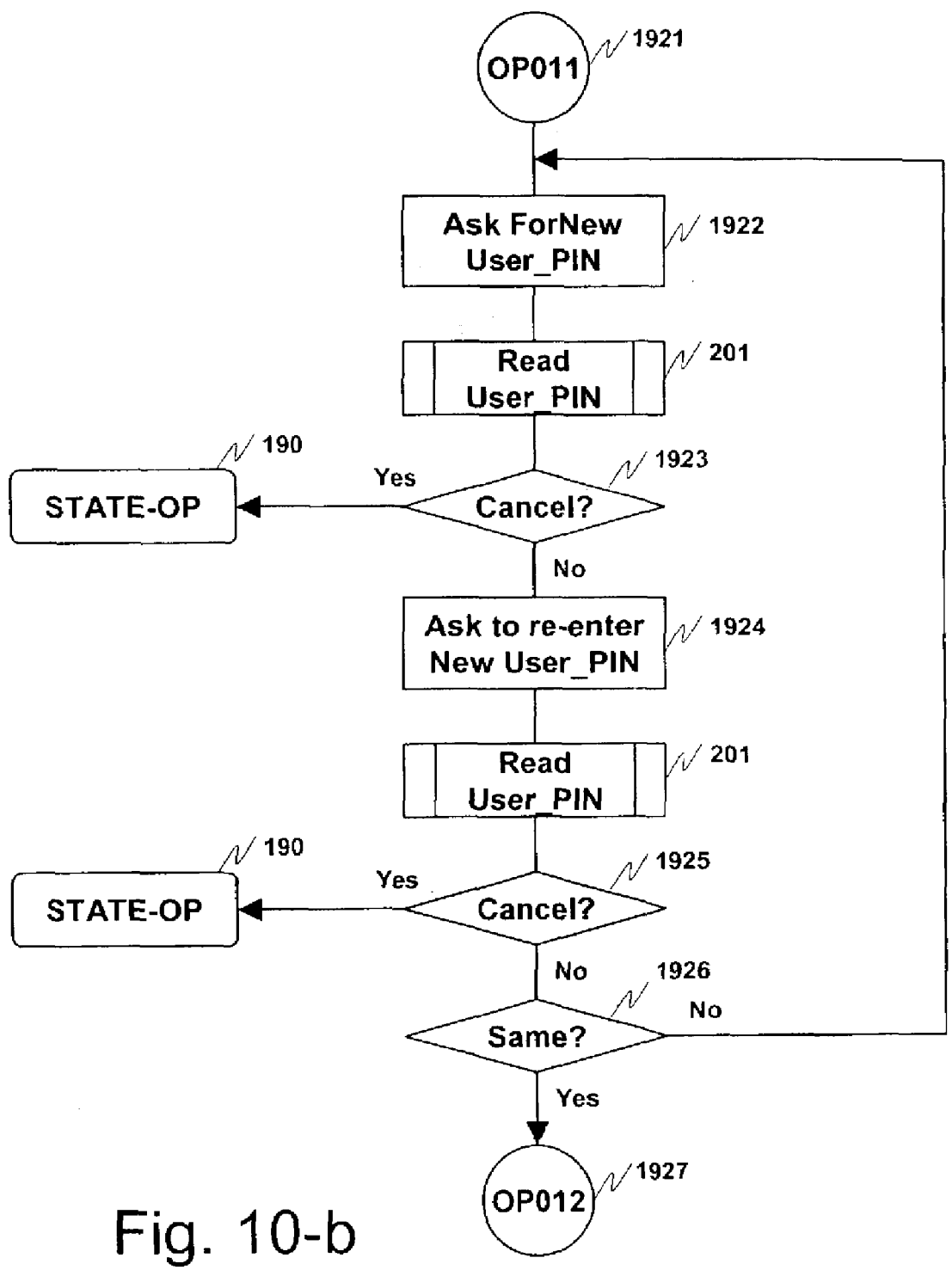
Fig. 10-b

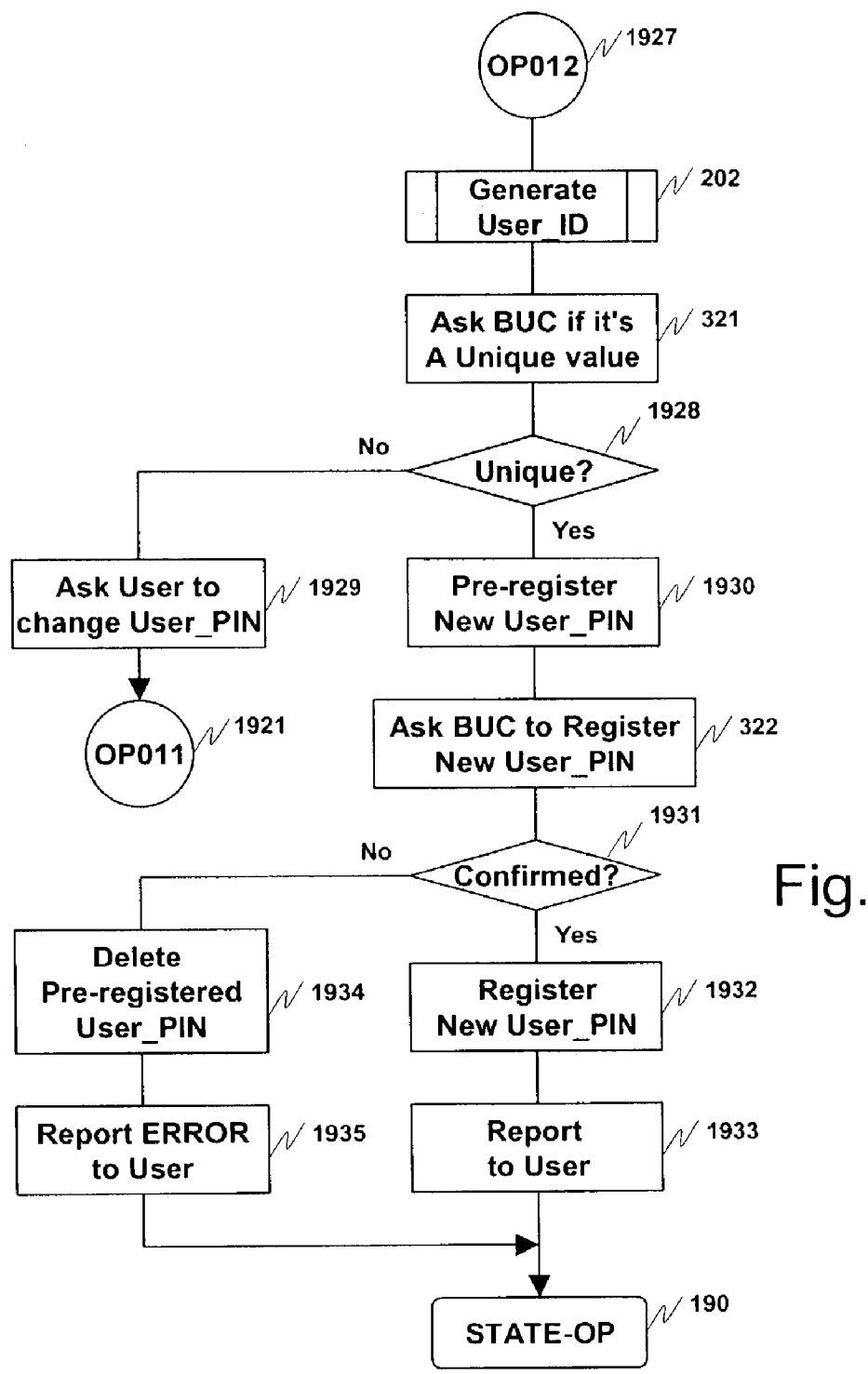
Fig. 10-c

HIDDEN DATA BACKUP AND RETRIEVAL FOR A SECURE DEVICE

FIELD OF THE INVENTION

The present invention relates to security in storing and stored information. The preferred or best mode environment is that of storage and backup of information in an authentication vicarious execution system that uses a secure device.

BACKGROUND OF THE INVENTION

The present invention relates to security during the access to a computer or computer information, particularly by the use of an agent, and the present invention relates to security in backing up information.

In general, an authentication vicarious execution system uses a secure device in the access of a computer or computer information.

There are many problems related to security with respect to authentication. Many services are offered on web sites of a WAN (Wide Area Network), for example, the Internet. The user who wants to receive these services will be registered at the web site, and at that time the user will decide upon or enter a previously decided upon user name and password, to log in. In many cases, the periodic modification of the password is not carried out because a password change is bothersome, although the password should be modified periodically.

To solve the problem of next bothersome repeated entry of a user name and password, the sign-on vicarious execution system was devised. Such a system provides considerably less complexity. In the use of the sign-on vicarious execution system, a person who wants to receive a service or other information over a network, discloses personal sign-on information. For example, the user discloses a name and password to an agent, for example a commercial company. The agent maintains registered records of its customer's unique user names and passwords. This company acts as an agent to consign the control of the sign-on information by having its sign-on vicarious execution control server provide the sign-on information to each site that the customer wishes to log on to, after the customer has once logged on to the sign-on vicarious execution control server. That is, having once signed on to the sign-on vicarious execution control server, the customer can access repeatedly web sites and have the sign-on information, user name and password, automatically provided by the agent without further complication or modification by the customer.

For security reasons, the sign-on information, or at least a portion of the sign-on information, should be changed periodically. Prior to the use of an agent, it was necessary for the user to contact each site in the network and change their sign-on information. With the use of an agent, the agent's customer needs to only once contact the agent, and thereafter the agent will automatically contact the sites that the customer has used and change the customer's sign-on information.

In addition to the specific sign-on information of a user name and password, there may be additional important personal information used to verify the authenticity, provide credit information, etc. of a particular user. It is understandable that users do not like to disclose this personal information to any individual of a company, for example the company managing the sign-on vicarious execution system, although the use of such a system to function as their agent is convenient. This hesitation is due to the risk that the personal information will leak outside of the sign-on execution company, for example through an attack from the outside, or through some human error or accident within the company, or by some other criminal type of behavior. Such a leakage is particularly dangerous, because the customer or user may not know the leakage has occurred, which is the usual case. There is a further risk involved with the entrusted personal information, in that the company may dissolve by bankruptcy or be purchased by another company, and in such cases the control of the information may pass to others not intended to obtain this information by the user.

That is, there is a general problem of securely storing information, without that information falling into unwanted hands.

There is a further problem involved in the leakage of such information, because once the personal information leakage has occurred and the information has gone to those to whom it is not intended, particularly with respect to a large-scale leakage, the correction of such a problem is voluminous in that the personal information of many people must be stripped from the sign-on vicarious execution system and possibly in addition stripped from other locations to where it has been sent.

There has been considerable interest in these problems and their solution, but problems still remain. It is the purpose of the present invention to address these problems.

U.S. Patent Application Publication US2002/0077992 A1, published Jun. 20, 2002, to Tobin, relates to a personal transaction device having a transaction privacy clearing house (TPCH), which authorizes a transaction based upon a device identifier and accessible data that includes account information of a user. If the secure device authenticates a user, then the secure device will execute a sign-on to each site requested by the user, that is it will act as the agent for the user. The user transaction device provides a device identifier when coupled to a transaction terminal. The secure device of the present invention may also be used as a sign-on agent and it supplies a device identifier when coupled to a transaction terminal.

In Tobin, the accessible data is stored in a public storage area of a memory storage device that can be communicatively coupled to the user transaction device. The user's personal transaction device is communicatively coupled to a detachable memory storage device. The detachable memory storage device includes both public and private storage areas. The encryption/decryption key for the private storage area is stored in the memory of the personal transaction device, that is the encryption/decryption key stays with the users personal transaction device, even if the detachable memory storage device is lost or stolen, and therefore the data within the private storage area that is encrypted would remain inaccessible within the personal transaction device that includes the key for the encrypted data. This patented system provides the user with good control over the personal information. Because the personal information and decryption codes are not concentrated, a large-scale information leakage cannot occur, that is, access is controlled and distributed by each user.

With the use of the Tobin sign-on agent, the authentication code, for example the password, may be long and complicated because it is sufficient for the user to remember only one password between the user and the secure device, and the secure device or agent provides the long and complicated authentication code.

U.S. Pat. No. 5,815,665, issued Sep. 29, 1998 to TEPER ET AL, relates to providing trusted brokering services over a distributed network, that is it relates to the use of an agent for providing sign-on information. The patented invention operates within an environment where the present invention is also usable. In such an environment, a Service Provider (SP) will host an accessible site on a distributed network, such as a WAN, for example the Internet, while relying upon a central on-line brokering service, the agent, to handle user authentication and billing matters. The user may employ or purchase the services or products of the SP, without repeatedly providing personal information, which personal information for sign-on is provided by the agent. With respect to purchasing, the personal information provided by the agent may include credit, billing and shipping information.

In TEPER et al, each user selects a password and is assigned a unique ID, which can be mapped to the user only by the agent, specifically in this case the online brokering service. The password and unique ID are stored in the brokering database, and there used to authenticate registered users.

The SP site sends a challenge message to the user's computer over the distributed network and the user computer responds by generating and returning a cryptographic response message. The cryptographic response message is preferably based on both the challenge message and the user's password, which is entered manually by the user. This response message is essentially meaningless to the SP site, but contains the information needed by the online brokering service to authenticate the user. The SP site forwards the response message to the online broker site along with the user's unique ID, which the SP site obtains from the user computer.

With the exception of the manual entry of the password by the user, this TEPER et al authentication sequence is transparent to the user. The user's computer temporarily caches the user password once it has been manually entered, allowing the user access to one SP site after another SP site without having to reenter the password.

The online brokering service also preferably stores and dynamically provides to the SP sites upon user authentication, user-specific customer data, which may include, for example, (1) user specified preferences for the display of certain types of data, (2) the geographic region (e.g., zip code) in which the user resides, or (3) the configuration of the user's computer.

An advantage mentioned by the TEPER et al patent is that the user can access the various SP sites and services using a single password and log on procedure, and can access one SP site after another without having to reenter the password. Another advantage is that the user is automatically provided with customized service, including customized access rights, at each registered SP site. These functions and advantages of TEPER et al are also provided by the present invention.

Prior to using the TEPER et al online brokering service, users and service providers must register with the online broker to establish a personal password that is known only by the user and the broker. Additionally, the broker assigns a unique ID that can be mapped to the user only by the broker. The system is suitable for use over a completely un-trusted public network, such as the Internet. The online broker maintains one or more databases that include the passwords, unique IDs, access rights and bills (charges) of the users during usage.

The response message of TEPER et al is a combination of the challenge message and the user password. Using a conventional one-way (that is non-reversible) hash algorithm, the challenge/password combination is converted into a hash code so that the service provider cannot extract the user's password. To authenticate the user, the online broker accesses the brokering database with the user's unique ID to look up the user's password and then determines whether the received response message corresponds to the user's password.

U.S. Patent Application Publication 2002/0112027 A1, published Aug. 15, 2002, to McHugh, et al, refers to difficulties that may arise for users who are conducting transactions on behalf of their employer or their company. In such cases, it is necessary for the individual user to have the requisite corporate information, including financial and billing information requested by a retailer or some other site. The present invention also addresses this security problem.

The McHugh et al patented system enables the user to store commonly requested data elements in a single location and to allow the user's device (for example a personal computer, mobile phone, PDA, or a web server of a trusted third party) to handle requests for data automatically, identifying and sending suitable information. This eliminates the time involved in repeatedly entering the same data into a number of different web sites or other data entry systems, and it also eliminates the potential for mistakes in typing or transcription of words or numbers, both of which are also advantages of the present invention.

As an example in McHugh, et al, a user operating from an un-secure device, for example a computer at an Internet Café, might direct the seller to a data server's web address for data to be supplied. The data server in response would send to the user, via the seller, a request for verification, for example to input a PIN, (Personal Identification Number), and only a successful response by the user to the seller (and from there to the data server) would enable the release of data. The present invention may operate in a similar environment.

Preferably, the McHugh, et al user interacts with the device at least partially by means of an ID device held by the user and an ID device reader connected to the un-secure device, for example at the Internet Café. The ID device may be selected from a magnetically readable data carrier, an optically readable data carrier, a carrier containing an integrated circuit on which identification is stored, a device operable to transmit electromagnetic signals to an ID device reader, and a mechanically readable data carrier. In paragraph 0107, the patent envisions the use of reversible encryption.

U.S. Pat. No. 6,378,075 B1, issued Apr. 23, 2002, to Goldstein, et al, relates to a trusted agent for electronic commerce. This patent involves leakage problems, through the agent and through the transmission of information between an agent and a web site, which problems are addressed by the present invention.

U.S. Patent Application Publication 2001/0044787 A1, published Nov. 22, 2001, to Shwartz, et al, relates to a secure private agent for electronic transactions. The published patent application addresses the security problem, and it appears to concentrate on the secure transmission of information between the agent and the requesting site.

U.S. Pat. No. 4,317,957, issued Mar. 2, 1982, to Sendrow, relates to a system for authenticating users and devices in online transaction networks, and is concerned with the encryption of private information in the central account and encrypted transmission of such data. Encrypting is used to authenticate the user. A remote terminal or computer employs multiple-encryption using a secret terminal master key stored in the terminal or computer to generate a working key that is used only to encipher the transaction request message that is generated within the terminal or computer. The account database is searched to find enciphered and other data corresponding to the account of the user and the device from which the message was received. It appears that the PIN is not stored at the user device or the retailer device. The terminal master key is never transmitted in any form.

The PCT application number WO 00/42540, published Jul. 20, 2000, to Markus, et al, further shows the environment of the present invention.

Therefore, there is a need for an improved security in the storage of information.

SUMMARY OF THE INVENTION

These and other needs are addressed by the present invention.

The objects of the present invention are to analyze the prior art vicarious authentication execution systems, to identify problems therein, to analyze the causes of such problems, and to provide solutions for the problems.

As a result of analyzing the prior art, the inventor has found: a need for storing information, originally or as a backup, so that it is secure against leakage; that the causes of past security problems relate to the information being in a form that it may be used as is or reconstructed and associated with the user of the storage; and provided a solution of encoding the data with a key that is not stored with the data and is irreversibly encrypted to provide a unique user ID that is stored as an index for the data along with a unique secure device ID.

Therefore, the present invention analysis of the prior art systems as to their problems and their causes has lead to the need for and the solution of a more effective and secure information storage system.

One problem with respect to the authentication vicarious execution systems of the prior art that use a secure device is that the data recovery is very difficult in case of theft or a missing secure device. The secure device may be missing due to loss, or theft, or destruction. With loss or theft, there is a possibility that personal information, such as the password, of the user is then leaked to those who would misuse it. Also, secure device recovery on the side of the user becomes more difficult.

To assist in the recovery of data, it is conceivable that the backup of the secure device is easy.

However, to disclose personal information, such as sign-on information, to the backup company produces almost the same risk as mentioned above with respect to disclosure of information to the agent. Therefore, the inventor has identified the problem of backing up information at a remote location. The cause of this problem, is that the agent's backed up information has a security problem of who controls the key of encryption and how the control of the key of encryption is maintained, even if various encryption systems are used to return information to a new secure device upon recovery of data from the backup storage.

Also, there is a problem of a portable secure device, for example, a user's laptop, having once been lost or stolen is a potential source of leakage. The solution is to nullify the previous secure device that has been stolen or lost, and the present invention addresses the problem of how to nullify such a secure device.

Therefore, the present invention relates to the backup of the personal information from the agent without the leakage of such personal information, details of the secure device, the restoring of the previous data into a new secure device, accessing the backup, and the nullifying of the previous secure device promptly in the event that the previous secure device has been lost, stolen or otherwise compromised.

In general, the user provides authentication information to an agent or a web site that then passes the information to an agent. The authentication information may be entered on the user's secure device or other device and include a user authentication code, for example a PIN, and in a wide sense includes a character string and other possible code expressions that may be aggregated and not limited to merely numerical entries. The authentication information may be divided into plural parts, for example a user name and a password.

The agent stores the user's personal information. This storage is preferably in encrypted form, with an encryption key. Unique user identification (user identifier) is generated by irreversible conversion from the encryption key in a secure device of the user. The irreversibly encrypted unique user identification and not the encryption key is transmitted to the agent. The user's secure device has a unique device number, which is also transmitted to the agent.

A backup storage is preferably remote with respect to both the user and the agent, but in any event located at a location that is not vulnerable to the same leakage, destruction and the like to which the agent's storage is subject. The backup storage associates the unique user identifier, the device ID, and the coded information in storage, as a single account. At the backup center, the coded information is accessed by a combination of the unique user identifier and the device ID. In the event of modifying the personal information, the coded personal information is obtained from the backup center through the use of the unique user identifier and the device ID, and then the coded personal information is de-encrypted by using the user PIN as the decryption key, so that the personal information may be used or may be modified. Modified personal information is sent to the backup center along with the unique user ID and the device ID, for storage.

In the event of a lost, stolen or otherwise compromised secure device or its storage, a new secure device or a new storage, generates the unique user identifier by irreversible encryption from the user PIN and downloads the encoded personal information from the backup center by using the unique user identifier. The personal information is returned to the backup center by the new secure device as valid encrypted information along with the unique new device identifier and the unique user identifier.

The user PIN is only temporarily stored in the user secure device. The user PIN is destroyed upon powering down of the secure device or by some command associated with an event such as the lapse of time with no activity or the logging off of a browser. Therefore, the user PIN is only temporarily stored and used in generating the unique user identifier and in encrypting or de-encrypting the encrypted information. The user PIN is never transmitted to or stored, permanently or temporarily, in the backup center. Therefore, even if the encrypted information is leaked, the user PIN is not available for de-encryption.

The encrypted information requires the unique user identifier for retrieval from storage or association with any particular user. The unique user identifier is irreversibly encrypted from the user PIN, and therefore the unique user identifier has no meaning by itself and the user PIN cannot be obtained from the unique user identifier.

The encrypted information requires the unique device identifier for retrieval from storage or association with any particular user's secure device. The device identifier is held and transmitted by the user's secure device itself, and if the secure device is lost, stolen or otherwise compromised, this device identifier is nullified upon the obtaining of a new secure device by the user. While the device identifier does appear in the storage of the backup center, the device identifier is used only for accessing the encrypted information at the backup center. After the encrypted information is stored again in the backup center with the use of a new device ID and a new or old unique user identifier, the previous device identifier is preferably nullified or removed from the backup storage. When there is renewal with a new secure device in the above manner, the backup center renews the device ID corresponding to the new user secure device and nullifies the previous device ID.

Therefore, no one who is not authorized can return to the personal information from the encoded information. This is true even if the encoded information is leaked, because it would not be leaked with the user PIN, which user PIN never exists at the backup center storage or temporarily. The encoded information itself cannot be misused because the encoded information has no meaning by itself, being encoded only by the user PIN, which user PIN is not associated with the encrypted information.

A secure device, for example a SIM (Subscriber Identity Module), may communicate by a mobile telephone according to the exemplary preferred embodiment. The joining information, for example, a contract phone number or a SIM account, etc., are strongly housed against an external access attack. The account information, phone number, etc., are transferred to a new terminal (secure device) when the SIM is removed from an old terminal and fixed to a different new terminal (secure device). The nonvolatile memory, such as flash memory, of the secure device, is on a chip. Therefore, the function of the SIM is taken over by the secure device. If an unauthorized person picks up a lost device, and tries to use the SIM as it is, the use of the information within the device is protected with the encryption function of the chip. Because of this, minimum misuse inhibition is needed only and some prior art has responded to this need, but as mentioned above not satisfactorily with respect to backup in particular.

The present invention is useful in other environments, for example in a world wide medical records system, wherein a user has the secure device as a wallet carried card, or a card or other data storage carried by a medical alert necklace, bracelet or the like. Upon entering a medical facility, for example an emergency room of a hospital, an ambulance or a doctor's office, the secure device would provide the secure device ID and the user would provide the user PIN voluntarily or without knowledge through another person or a carried identification in the event that the user is incapacitated. The secure device would irreversibly encrypt the user PIN. The encrypted user ID and the device ID are then sent to a world wide central location, for example over the internet, to provide valuable medical records to assist the medical personal in providing diagnosis and treatment. The stored records at the center, backup center, include encrypted information that could not be decrypted without the PIN and the PIN cannot be extracted from the irreversibly encrypted user ID. Thus the records are secure even if leaked.

The present invention is useful in a world-wide general data storage system, wherein a user has the secure device as a wallet carried card, or a card or other data storage easily connected to a computer or as a permanent part of a computer terminal, for example a laptop. Upon wanting to store or backup files, the secure device would provide the secure device ID and the irreversible encryption of the user PIN, after the secure device irreversibly encrypted the user PIN. The encrypted user ID and the device ID are then sent to a world wide central storage location, for example over the Internet. The stored records at the storage center, the backup center, include encrypted data such as documents, drawings, graphics and the like that could not be decrypted without the PIN and the PIN cannot be extracted from the irreversibly encrypted user ID. Thus the records are secure even if leaked.

Still other aspects, features, and advantages of the present invention are readily apparent from the following detailed description, simply by illustrating a number of particular embodiments and implementations, including the best mode contemplated by the inventor for carrying out the present invention. The present invention is also capable of other and different embodiments, and its several details can be modified in various obvious respects, all without departing from the spirit and scope of the present invention. Accordingly, the drawing and description are to be regarded as illustrative in nature, and not as restrictive.

BRIEF DESCRIPTION OF THE DRAWINGS

The present invention is illustrated by way of example, particularly a preferred embodiment best mode, and not by way of limitation. Further objects, features and advantages of the present invention will become more clear from the following detailed description of a preferred embodiment and best mode of implementing the invention, as shown in the figures of the accompanying drawing, in which like reference numerals refer to similar elements, and in which:

FIG. 5A is a flow chart of the processing of STATE-02, of FIG. 2, for the opening of a new account for the user with the agent;

FIG. 5B is a synchronized timing chart of some of representative communications between the user, the user's secure device, a certification authority and the backup center during the processing of FIG. 5A.

FIG. 6A is a flow chart of the processing of STATE-03, of FIG. 2, for the renewal of account personal information;

FIG. 6B is a synchronized timing chart of the communications between the user, the user's secure device, a certification authority and the backup center during the processing of FIG. 6A;

FIGS. 10A, 10B and 10C are together a flow chart of one process of STATE-00, of FIG. 2, particularly to change a user PIN.

DESCRIPTION OF THE PREFERRED EMBODIMENT

Figure 1:
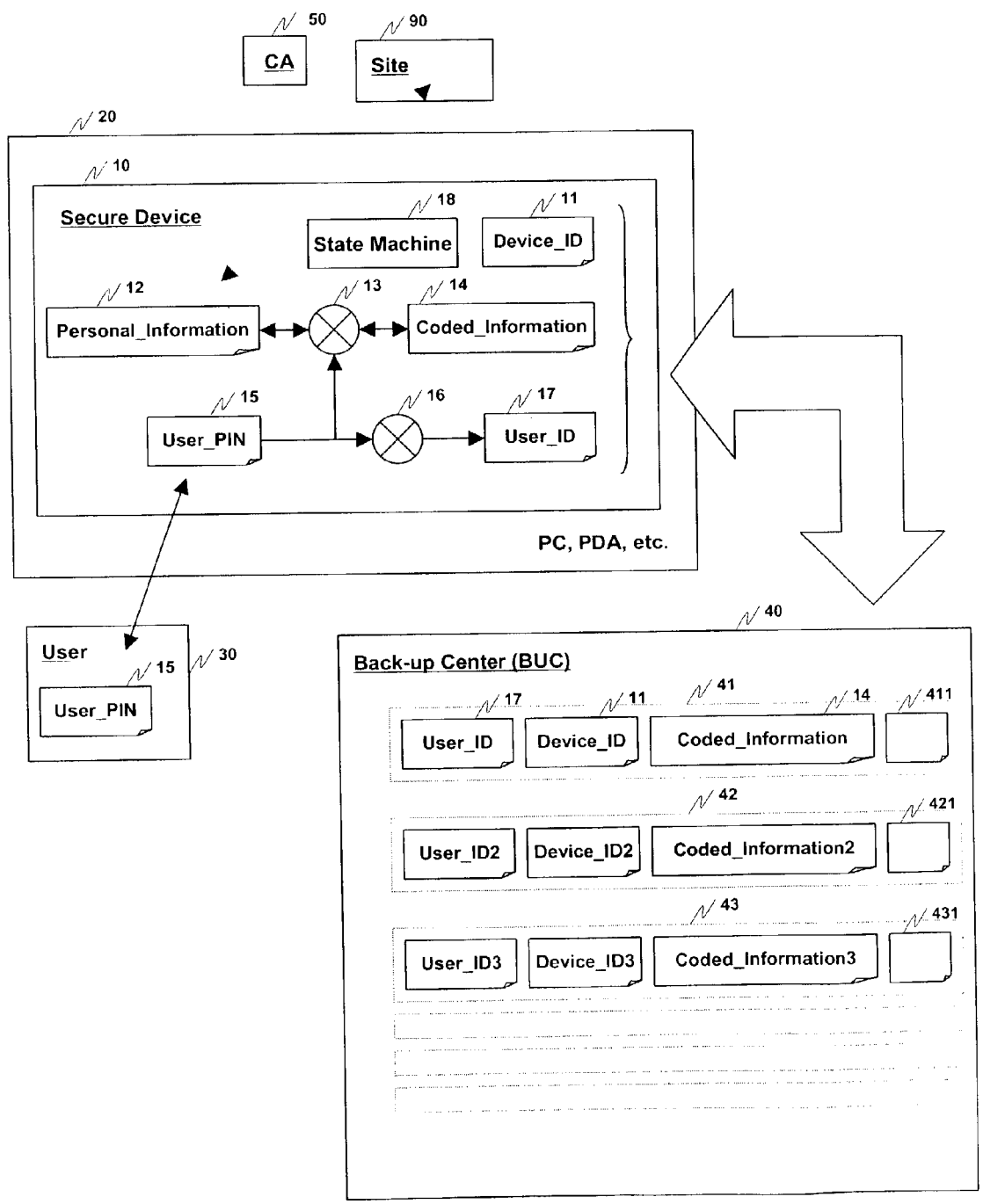
FIG. 1 is a schematic of the overall system of the present invention.

The embodiment is described as a system, method, hardware, computer media and software.

In the following description, for the purposes of explanation, numerous specific details are set forth in order to provide a thorough understanding of the broader aspects of the present invention, as well as to appreciate the advantages of the specific details themselves according to the more narrow aspects of the present invention. It is apparent, however, to one skilled in the art, that the broader aspects of the present invention may be practiced without these specific details or with equivalents determined explicitly herein or in accordance with the guides set forth herein. Well-known structures and devices are shown in block diagram form in order to avoid unnecessarily obscuring the present invention with unnecessary details.

The present invention is also capable of other and different embodiments, and its several details can be modified in various respects, all without departing from the spirit and scope of the present invention. The drawing and description are illustrative and restrictive.

FIG. 1 shows an exemplary embodiment for the authentication vicarious execution system, where a user 30 has a secure device 10 that communicates with a backup center, directly or indirectly through an agent, for example, a web site of a service, information or product provider and/or through a certification authority. The secure device 10 and the user 30 attest by sending a user PIN 15 to a remote location, for example a web site that in turn sends it to an agent, or directly to the agent itself.

The state machine 18 controls the secure device 10.

Usually, the secure device 10 is coupled or docked with the information processing terminal 20, such as a Personal Computer (PC) or Personal Digital Assistant (PDA). The information processing terminal 20 has a suitable input, for example a keyboard, a touch screen, an audio interface, a mouse, a LAN (Local Area Network) or WAN (Wide Area Network), or the like. Further, the information processing terminal 20 has a suitable interface with the secure device 10, which could be any device for transmission of data, for example a cable, a direct plug-in, Fire Wire (IEEE 1394), IR (Infra Red), RF (Radio Frequency), USB (Universal Serial Bus), magnetic card reader, optical card reader, PC-Card (Standardized by PCMCIA (Personal Computer Memory Card International Association) and JEITA (Japan Electronics and Information Technology Industries Association)) or the like card connectors or Ethernet, or other wireless communication either close coupled or as a part of a LAN (Local Area Network) or WAN (Wide Area Network). Although it is desirable that the input and coupling are protected with respect to security of transmission of data and unexpected access, other than by the features mentioned herein, this is not a required condition of the present invention.

The secure device 10 may be a magnetically recorded computer readable data carrier, an optically recorded computer readable data carrier, a carrier containing an integrated circuit having recorded thereon computer readable data, a computer readable data storage medium operable to transmit electromagnetic signals to an ID device reader, and a mechanically readable computer readable data carrier.

The secure device 10 has a computer readable memory storage that includes both public and private storage areas. The encryption/decryption key, PIN 15, may be stored only in the private storage area so that it stays with the secure device 10, even if the secure device 10 is lost or stolen, and, if desired, the key may be erased upon powered down when the secure device is decoupled from the terminal 20. This system provides the user with good control over the encryption/decryption key, PIN 15 and a leakage of the encryption/decryption key, PIN 15 cannot occur.

The present invention is usable even if the user PIN 15 is a single authentication code, but according to the preferred exemplary embodiment, the authentication code provided by the user is a set of plural information, including for example, a user name and a user password (PIN), which together comprises a user PIN 15. That is, as to the present invention, the term user PIN refers to a code, not necessarily encrypted, that may be a combination of meaningful parts and/or meaningless parts.

The user only needs to know one principle authentication code, PIN 15, in order to send authentication from the unique secure device 10 to a remote location, and therefore this authentication code, PIN 15, may be a complicated and long code, for example to include a part of a poem, because the authentication code is only entered once by the user 30. The agent, at least partially including the software stored permanently on the secure device 10 will supply personal information as needed to various web sites 90, certification authority 50 and the like without reentry of an authentication code each time the user enters a new site. The secure device 10 temporarily caches or permanently stores in a private storage portion of memory the user PIN 15 once it has been manually entered, allowing the user access to one SP site after another SP site without having to reenter the PIN 15.

The user 30 has control over the user PIN 15. The user PIN 15 never leaks to others, because: the user PIN 15 is preferably only temporarily held by the secure device 10 and automatically deleted upon power down of the secure device 10; and/or the PIN 15 is deleted when it is no longer needed, for example no longer needed to authenticate a particular session, after it has been used for a particular session with the user 30; and the user PIN is not transmitted to the backup center BUC 40, rather it is the user ID 17 that is transmitted. In FIG. 1, the user ID generator 16 generates user ID 17 by irreversible encryption or conversion from the user PIN 15. Therefore, it is not possible to regenerate the user PIN 15 if only the irreversibly encrypted user ID 17 is known. The user ID generator 16 may employ a known hash function, or any other irreversible encryption.

The secure device 10 has a unique secure device ID 11 that is stored in nonvolatile memory within the secure device 10. The device ID 11 is a unique number assigned to each secure device 10 individually, for example at the time of manufacture and the unique secure device ID 11 may be a product serial number. Alternatively, the unique secure device ID 11 is a number produced indirectly by some conversion from a device unique secret key.

By way of example, the personal information 12 contains a set of data that may include one or more of the user name, a password, a URL address of a user's web site, the user email address, credit or debit card information, mailing address, telephone number, national of social security number, user specified preferences for the display of certain types of data, the geographic region (e.g., zip code) in which the user resides, the configuration of the user's computer and other sign-on information that may be desired by various web sites on the Internet.

The information cipher processor 13 encodes the personal information 12 into coded information 14, using the user PIN 15 as an encryption key, preparatory to sending the encrypted information 14 to the backup center BUC 40. The information cipher processor 13 also decodes the coded information 14 into personal information 12 using the user PIN 15 as a decryption key, after the coded information 14 has been returned by the backup center BUC 40 for a purpose such as confirmation, renewal and the like.

The secure device 10 is coupled with the backup center BUC 40 over a transmission line that may be a LAN (Local Area Network) or WAN (Wide Area Network), or the like. Further, according to the broader aspects of the present invention when the backup center is merely remote or local, primary or backup storage, for ordinary computer usage, the transmission line of the coupling to the user secure device may be a LAN (Local Area Network) or WAN (Wide Area Network), a cable, a direct plug-in, Fire Wire (IEEE 1394), IR (Infra Red), RF (Radio Frequency), USB (Universal Serial Bus), magnetic card reader, optical card reader, PC-Card or the like card connectors, Ethernet, or other wireless communication. Although it is desirable that the coupling is protected, other than by the features mentioned herein, with respect to security of transmission of data and unexpected access, this is not a required condition of the present invention.

The backup center 40 has a database or other storage that contains a plurality of separate account records, or more simply accounts, 41, 42, 43, etc. Normally, the accounts 41, 42, 43, etc correspond respectively to a plurality of customers of the vicarious execution system, or more broadly customers of a backup or primary storage facility; but also, some customers may have more than one account, with different user IDs 17 and preferable different device identifiers 11. Each account record has exemplary fields of user ID 17, device ID 11, coded information 14, and control information (411, 421, 431, etc.) as needed. The control information may serve various purposes, for example it may include accounting information important internally to the backup or storage center.

Between the user 30 and the secure device 10, the sole confirmation of user identity or authentication is the unique user PIN 15. Between the secure device 10 and the backup center 40 the sole confirmation of user identity or authentication is the pair of irreversibly encrypted unique user ID 17 and unique user secure device ID 11. The backup center 40 is unable to regenerate the unique user PIN 15 from the irreversibly encrypted unique user ID 17, because the irreversibly encrypted unique user ID 17 is generated by irreversible conversion from user PIN 15, as mentioned above. Because of this, the personal information 12 cannot be regenerated from the coded information 14 by using user ID 17. In other words, even if the data (irreversibly encrypted unique user ID 17, unique user secure device ID 11, and coded information 14) of the backup center is leaked, no one can use this data in a form that has any meaning.

Figure 2:
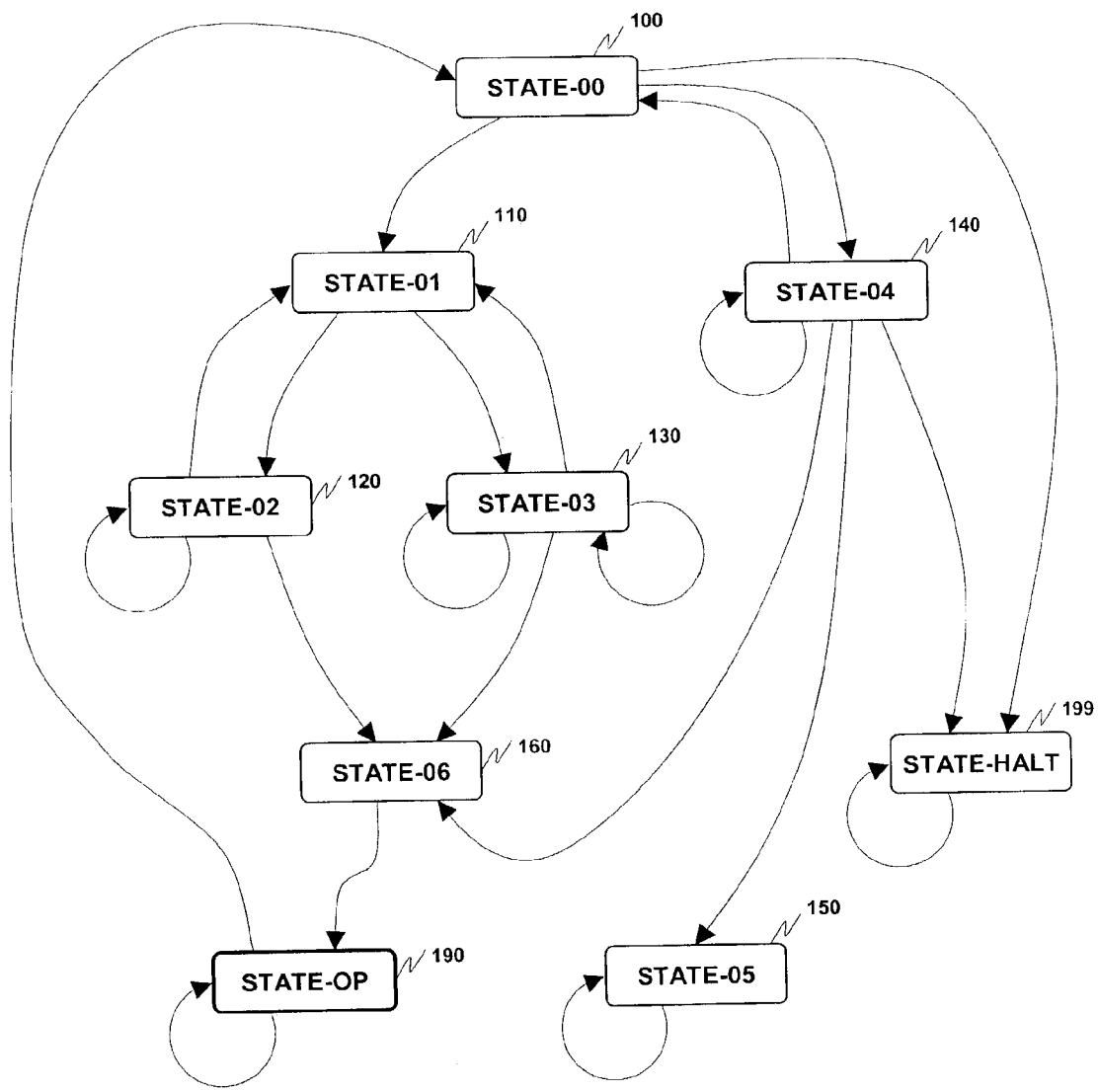
FIG. 2 is an exemplary state transition diagram that shows the flow of processing between various representative states of the state machine of FIG. 1.

FIG. 2 discloses an exemplary state transition diagram of the state machine 18 of FIG. 1.

STATE-00, process 100, is the initial state that the state machine 18 enters when power is supplied or when the user 30 logs on. The state machine makes a decision as to whether or not the processing sought is to be that of a first use or site logon with authentication and directs further processing to either STATE-01, process 110, or STATE-04, process 140, respectively. The decision may be based upon a user response to a query from the user secure device 10 to the user or based upon the condition of a permanently stored flag that is set the first time that the user secure device 10 successfully completes a first use processing. STATE-00, process 100, is further disclosed in the flow chart of FIG. 3.

STATE-01, process 110, is the condition that secure device 10 enters for first time usage, after factory forwarding, and the process directs whether the first use is one of establishing a new account at the backup center 40 or merely one of renewing an old account with new information, for example for a new secure device 10 to replace a lost previously used secure device 10 or renewing the account with a changed user ID 15, for example a new password. STATE-01, process 110, is further disclosed in the flow chart of FIG. 4.

STATE-02, process 120, is the condition to register a new account for the user secure device 10. Following the process of STATE-02, the state machine enters STATE-06, process 160. STATE-02, process 120, is further disclosed in the flow chart of FIG. 5A and the timing diagram of communications of FIG. 5B.

STATE-03, process 130, is the condition of renewal of an old account with new or revised personal information 12. Following the process of STATE-03, the state machine enters STATE-06, process 160. STATE-03, process 130, is further disclosed in the flow chart of FIG. 6A and the timing diagram of communications of FIG. 6B.

STATE-04, process 140, is the state condition of identification of the user 30 and confirmation of the identity that is user authentication processing or logon. STATE-04, process 140, is conducted after STATE-01, process 110. Decisions are made as to whether to return to the beginning of STATE 00 or STATE 04, and whether there is further processing proceeding with STATE-06 for initialization or to STATE-05 for backup of the personal information 12, or to STATE-HALT, process 199, to halt further processing. STATE-04, process 140, is further disclosed in the flow chart of FIG. 7.

STATE-HALT condition, process 199, nullifies the secure device 10 so that it has no further function.

STATE-05, process 150 is, for example, the condition when the personal information 12 inside the secure device 10 is backed up in the form of encrypted (coded) information 14, for example from a personal information kiosk terminal, etc. STATE-05, process 150, is further disclosed in the flow chart of FIG. 8.

STATE-06, process 160, is reached from one of the STATE-02 or STATE-03 or STATE-04. The condition of STATE-06, process 160, is disclosed in more detail in the flowchart of FIG. 9.

STATE-OP, process 190, is performed either as STATE-OP-01 or STATE-OP-02, or it may be performed as other conditions not needed to be disclosed for an understanding of the present invention. STATE-OP is reached thru the path of logon authentication by user 30 that is established with the user PIN 15 in STATE-04, process 140 and the initialization of the STATE-06, process 160, during the condition of initialization with the secure device 10. Alternatively, STATE-OP, process 190, is reached thru the path from STATE-06 after the first use processing of STATE-01 and either STATE-02 or STATE-03.

STATE-OP-01, of STATE-OP, process 190, carries out the vicarious execution processing of the user 30 that uses personal information 12. Upon failure of the power supply, exceeding a specific log on time restriction or time out, or the intended log off by the user, the secure device 10 returns to STATE-00, process 100. STATE-OP-01 is further disclosed in the flow chart of FIGS. 10A, 10B and 10C, process 1910, to provide a change in the user PIN. STATE-OP-02 is further disclosed in the flow chart of FIG. 11, process 1940, for coded information backup.

Figure 3:
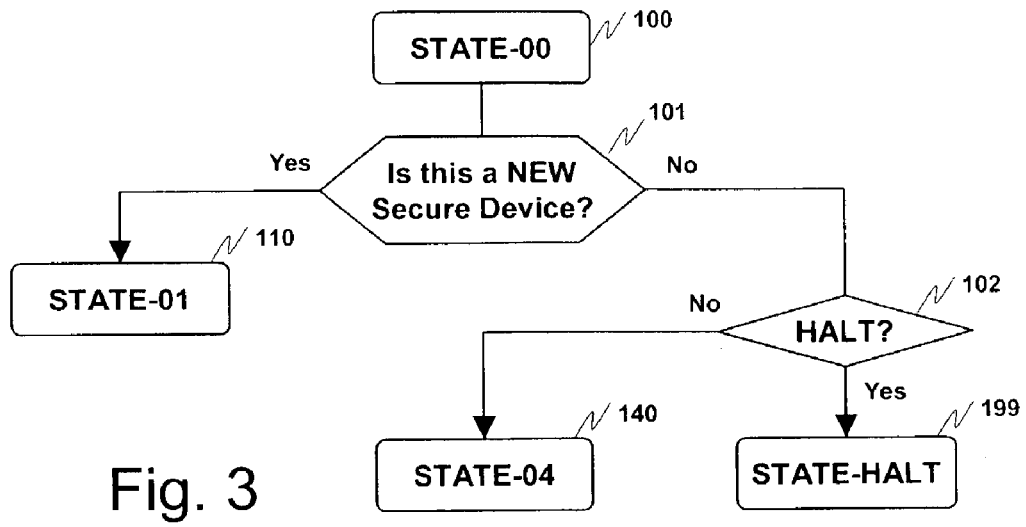
FIG. 3 is a flow chart of the processing of STATE-00, of FIG. 2, for power-on of the user's secure device.

FIG. 3 is an exemplary transition flowchart of STATE-00, process 100, as performed by the state machine 18 of FIG. 1, as a part of the state transitions of FIG. 2.

STEP 101 judges, with a conditional judgment 101, if the user secure device 10 is in the condition of first use directly after the time of factory forwarding or whether the condition is one of already having being initialized by the user 30. This decision may be based upon an input from the user 30 after inquiry by the user secure device 10 or according to a flag set within the secure device when the secure device 10 fetches its device ID 11 for the first time or after the first pass through the STATE 06 of initialization, process 160 of FIG. 2.

STEP 110 is reached in the case where the condition of the secure device 10 is at the time of factory forwarding. The state machine 18 then performs STATE-01, process 110, which is further described with the flow chart of FIG. 4.

STEP 102 is reached when the secure device 10 was initialized previously, with the initialization being performed by the STATE 06 of FIG. 2. The condition judgment 102 judges and accordingly moves the processing to STATE-04, process 140, if the secure device 10 is not halted, and otherwise moves to STATE-HALT, process 199 of FIG. 2.

STEP 199, the STATE-HALT condition, process 199, nullifies the secure device 10 so that it has no further function.

Figure 7:
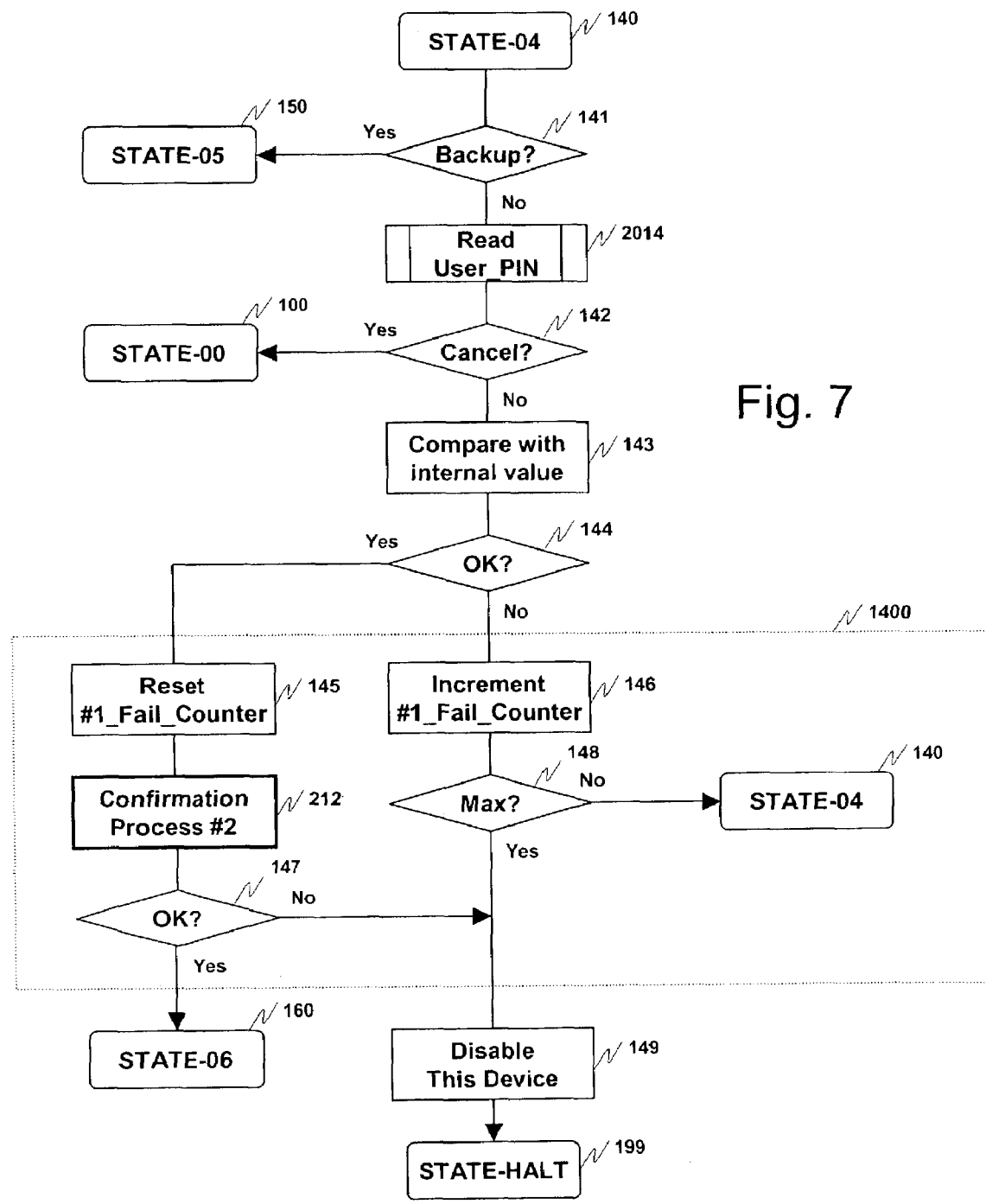
FIG. 7 is a flow chart of the processing of STATE-04, of FIG. 2, for user authentication upon log-on by the user.

STEP 140 provides for user 30 logon and authentication, which are further described with respect to the flow chart of FIG. 7.

Figure 4:
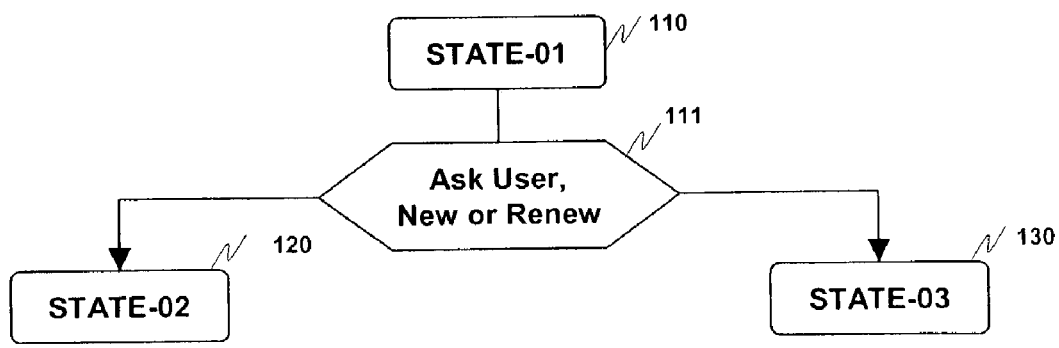
FIG. 4 is a flow chart of the processing of STATE-01, of FIG. 2, upon first use of the secure device.

FIG. 4 is an exemplary transition flowchart of STATE-01, process 110, as performed by the state machine 18 of FIG. 1, as a part of the state transitions of FIG. 2.

STEP 111 inquires of the user 30 whether the first use is to establish a new account or to renew an existing account with the new secure device, and then awaits for the user input. In more detail, when the user 30 couples the secure device 10 to the information terminal 20, the secure device 10 inquires of the user 30 if this operation is a new registration or renewal, which inquiry is made through the information terminal 20, as the decision 111 of FIG. 4. Alternatively, the application program on information terminal 20 may inquire of the user 30 and make the decision 111.

STEP 120 is reached to register a new account by establishing a new account in the backup center 40, with secure device 10 in the condition at the time of factory forwarding. At this time, only device ID 11 is recorded in the secure device 10, it being permanently stored at the time of manufacture. The state machine 18 then performs STATE-02, process 120, which is further described with respect to the flow chart of FIG. 5. The secure device 10 commands a new registration to backup center 40, when decision 111 determines that the user 30 wants to perform a new register, to thereby obtain the new account.

FIG. 5A is an exemplary transition flowchart of STATE-02, process 120, as performed by the state machine 18 of FIG. 1, as a part of the state transitions of FIG. 2.

STEP 2012 requests the user 30 to input their user PIN 15 and the secure device 10 waits for and then reads the user input, which may be the requested user PIN 15 or a cancel command. The user PIN 15 may be defined by the aggregation of a plurality of authentication codes, for example a user name (PIN) and user password (PIN), STEP 2012 involves the first communication that is shown in FIG. 5B, from the user 30 to the secure device 10.

STEP 121 returns to STATE-01, step 110, by conditional judgment 121 when the user 30 inputs a cancel command. When the PIN 15 is input, processing flows to step 2022.

STEP 110 performs the processing of STATE 01 according to the flowchart shown in FIG. 4, which is performed by the state machine 18 of FIG. 1.

STEP 2022 generates the user ID 17 by irreversible conversion from the user PIN 15 that was received in step 2012, by using the ID generator 16 of FIG. 1.

STEP 321 inquires of the backup center whether or not the user ID17 is already registered at the backup center 40, that is inquires if the user ID 17 (and thus effectively whether the user PIN 15 from which it is derived is also unique, although the backup center does not know the user PIN 15). STEP 321 involves the second communication that is shown in FIG. 5B, from the secure device 10 to the backup center BUC 40.

STEP 122 receives the answer to the inquiry of step 321 and accordingly judges whether the user ID 17 is unique at the backup center. STEP 122 involves the third communication that is shown in FIG. 5B, from the backup center BUC 40 to the secure device 10.

STEP 125 is run when conditional judgment 122 determines that the user ID 17 is the same as a currently active user ID. The step 125 requests the user 30 to input different user identification, which is the user PIN 15 in the example. After the input of a different user ID 15, the processing of the state machine 18 returns to STATE-02, step 120. In the case of an aggregation of more than one user PIN, for example a user name (PIN) and user password (PIN), there is the ability for the user to modify the user PIN 15 that was not a unique value, with modification of only a portion of the aggregated authentication code, for example modification of the user password (PIN).

STEP 123 is run when conditional judgment 122 determines that the user ID 17 is not the same as a currently active user ID, that is determines that the user ID 17 is unique. Inquiry is made of the user to confirm correctness of the user PIN 15 that was received in step 2012. If there is no confirmation, step 125 is run.

STEP 125 is run when conditional judgment 123 determines that the user 30 did not confirm the user ID or PIN 15. The step 125 requests the user 30 to input different user identification, which is the user PIN 15 in the example. After the input of a different user ID, the processing of the state machine 18 returns to STATE-02, step 120. Even in the case of an aggregation of more than one user PIN, for example a user name (PIN) and user password (PIN), there is the ability for the user to modify the user PIN 15 that was a unique value, by refusing to confirm in step 123 and with modification in step 125 of only a portion of the aggregated authentication code, for example modification of only the user password (PIN).

STEP 124 pre-registers the user PIN 15 in a volatile portion of the memory of the secure device 10, where it will be lost upon power down.

STEP 322 requests that the backup center 40 register the user ID 17 and the device ID 11 as indexing identifiers of a new account. STEP 322 involves the fourth communication that is shown in FIG. 5B, from the secure device 10 to the backup center BUC 40.

STEP 126 waits for confirmation from the backup center that the new account has been established and that both of the irreversibly encrypted user ID 17 and the device ID 11 have been register to identify the new account, Step 126 passes further processing to step 127 when there is confirmation from the backup center BUC 40 and passes further processing to step 126 when there is no confirmation from the backup center BUC 40. STEP 126 involves the fifth communication that is shown in FIG. 5B, from the backup center BUC 40 to the secure device 10.

STEP 127 registers user PIN 15 in a non-public or secure portion of the memory of the secure device 10 and removes the pre registration storage of step 124. With this, the establishment processing of the new account is at an end. Further processing is then passed to STATE-06 for initialization as shown in the state transition diagram of FIG. 2 and shown in more detail in FIG. 9.

STEP 128 is reached in the case where the confirmation of from the backup center 40 was not obtained. The pre-registration of the user PIN 15 of step 124 is cancelled, that is the cancellation of the temporary registration of user PIN 15.

STEP 129 provides notification to the user 30 that the registration has failed. The notification may be through the terminal 20 and/or by way of an email message, for example. Then, the secure device 10 changes the state of the state machine 18 to that of STATE-02, step 120, which is a return to the start of processing in FIG. 5A, for establishment of a new account, as shown in the state transition diagram of FIG. 2.

FIG. 5B sets forth the timing of some of the communication operations of the components of FIG. 1, for the session of the normal new account registration as explained above with respect to the flow chart of FIG. 5A. As seen in FIG. 5B, for user PIN 15 registration into the secure device, the user 30 first communicates the user PIN 15 to the secure device 10. Then the secure device 10 irreversible encrypts the user PIN 15 into the user ID 17, which user ID 17 is directly sent to the backup center BUC 40. The backup center pre-registers the new user ID 17 and communicates or confirms this pre-registration along with an identification of the user ID 17 in a transmission to the secure device 10. This transmission confirms the uniqueness of the user ID 17. Thereafter, the secure device 10 transmits the secure device ID 11 to the backup center 40. The backup center then registers the new user ID 17 together with the device ID 11 to establish an account record for the user, and then the backup center confirms such registration to the secure device 10.

FIG. 6A is a flow chart of the first use operation for renewal of an existing account, which corresponds to the renewal STATE-03, process 130, of the state machine 18, as set forth in FIG. 2. The renewal is according to the timing of communications as set forth in the timing diagram of FIG. 6B.

STEP 130 starts the renewal process, which is reached from the branching of FIG. 4.

STEP 2013 requests the user 30 to input their user PIN 15 and the secure device 10 waits for and then reads the user input, which may be the requested user PIN 15 or a cancel command. The user PIN 15 may be defined by the aggregation of a plurality of authentication codes, for example a user name (PIN) and user password (PIN), STEP 2013 involves the first communication that is shown in FIG. 6B, from the user 30 to the secure device 10.

STEP 131 performs a decision as to whether or not to cancel a renewal process. If the User 30 inputs a cancel command, processing proceeds to STATE-01, which is operation 110 of FIG. 2 for the state machine 18. When the PIN 15 is input, processing flows to step 2023.

STEP 2023 irreversibly generates the encrypted user ID 17 when the secure device 10 encrypts the entered user PIN 15, which was entered as the first communication of FIG. 6B. STEP 2023 generates the user ID 17 by using the user ID generator 16 of FIG. 1.

STEP 331 provides an inquiry to the backup center 40, to inquire of the backup center 40 whether or not there already exists a user ID 17 corresponding to the user ID 17 generated by STEP 2023 (and thus effectively whether the user PIN 15 from which it is derived is also unique, although the backup center does not know the user PIN 15). STEP 331 involves the second communication of FIG. 6B from the secure device 10 to the backup center BUC 40.

STEP 133 determines, according to the response from the backup center in answering the inquiry of step 331, whether there is a match between the user ID 17 generated in STEP 2023 and sent to the backup center 40 in STEP 331 with a user ID 17 already existing in an account stored at the backup center 40. When there is no match, processing proceeds to STEP 134, and when there is a match, processing proceeds to STEP 332.

STEP 134 asks the User 30 to check the user PIN 15, that is, to reenter the user PIN 15 in the event that the previously entered user PIN 15 was inadvertently miss-entered. Thereafter processing returns to STEP 130, which is the beginning of STATE-03, of the state machine 18.

STEP 332, as seen in FIG. 6B, with respect to the third communication, downloads the coded/encrypted information 14 from the backup center BUC 40 to the secure device 10, in accordance with a command from the secure device 10 to the backup center 40 commanding such a download. Preferably, the backup center 40 places the current account in a reservation condition, in addition to sending the coded information 14.

STEP 135 is performed by the secure device 10 in trying to regenerate the personal information 12 from the coded information 14 by using the user PIN 15 as a the encryption key. For this purpose, the user PIN 15 may be that first entered with the first transmission of FIG. 6B, which is later erased from temporary memory of the user secure device 10 at power down. Alternatively, STEP 135 may first command the User 30 to reenter the user PIN 15, which provides additional security, but at the expense of convenience.

STEP 136 reaches a decision as to whether or not the personal information 12 that was decoded in step 135 is correct, by providing an inquiry of the user 30 and waiting for a confirmation from the user 30. In the event of a confirmation, processing proceeds to STEP 333, and if there is no confirmation in step 136, processing proceeds to STEP 334.

STEP 334 first transmits an error message to the backup center 40 (the simplified timing diagram of FIG. 6B does not show all of the communications). The notification may be through the terminal 20 and/or by way of an email message, for example. Then processing returns the state machine to the beginning of STATE-03, which is STEP 130 of FIG. 6A.

STEP 333 first nullifies the previous device ID 11, that is, the device ID 11 number that corresponded to the lost secure device 10 is nullified. The device ID 11 of the new secure device 10 is transmitted to the backup center, as seen in FIG. 6B as the third communication, with a command for the backup center to register the device ID 11 of the new secure device 10 with the current account to replace the previous device ID 11 of that account. This is normal processing according to the previous preferred example decision that the personal information 12 was regenerated normally using the user PIN 15 as the decryption key, to de-encrypt the coded information 14.

STEP 211 is a confirmation process that typically involves a certification authority, CA 51 in FIG. 6B, checking the personal information 12 and the identifiers 11, 17, and thereafter sending of a confirmation code 63 according to communication 2111, of FIG. 6B. The confirmation code 63, for example, is sent by email to the user 30, and the confirmation code 63 requests that the user 30 confirm. The user confirmation is transmitted to the certification authority CA 51 as a return of the confirmation code 63, etc. according to communication 2112 of FIG. 6B, which may be by email. The certification authority, in response to receiving the encrypted information, de-encrypts the encrypted information, extracts a destination (such as the E-mail address of the user) other than the secure device 10 from the de-encrypted information and sends the confirmation code 63 to the destination; thus blocking providing the encrypted information to the user through the secure device without confirmation in view of the absence of the secure device ID.

After STEP 333, wherein the new device ID 11 is sent to the backup center, the backup center registers the new device ID as mentioned, and then the backup center waits for the confirmation of step 211. As seen in FIG. 6B, user confirmation of STEP 211 may involve a transmission of the encrypted user ID 17, the device ID 11 of the new device, an e-mail address 61, and, of course, the address for the backup center in a message sent to a separate certification authority CA 51 that is called in to mediate the process. In an authentication method that uses PKI (Public Key Infrastructure), the informer of information trusts a confirmation that is certified by the certificate authority CA 51. The certificate authority CA51 is a third party mediating between the secure device 10 and the backup center 40. The secure device 10 and the backup center 40 usually communicate with mutual justifiability by the intervention of the certification authority CA 51. However, it is also conceived that the certification authority SA 51, may in fact be the same as the backup center 40 instead of being an independent institution. The certification authority CA 51 sends communication 2113, of FIG. 6B, to the backup center BUC 40, as shown in FIG. 6B.

STEP 137 registers the device ID 11 of the new secure device 10 together with the user ID 17 and the encrypted information 14 as a renewed account at the backup center, for the current secure device 10. Upon receipt, the backup center cancels the reservation condition of the account. Thereafter, the state machine returns to STATE-06, operation 160 of FIG. 2.

According to one example, the personal information 12, encoded as encoded information 14 and stored at the backup center 40, preferably includes the e-mail address of the User 30. Therefore, when the secure device 10 receives the coded information 14 downloaded from the backup center according to STEP 135 of FIG. 6A, the e-mail address may be extracted from the personal information 12 that was decoded from the encoded information 14 using the PIN 15 as the decryption key. Therefore, in STEP 211, the secure device may perform the confirmation and send the certification authority the mentioned information of user ID 17, device ID 11, e-mail address 61 and backup center address 62 automatically without entry of information at this step by the User 30.

The confirmation transmission 2111 provided by the certificate authority to the user, preferably through e-mail, will involve a confirmation code 63 generated by the certificate authority 51. Thereafter, a transmission 2112 is sent from the User 30 to the certificate authority CA 51, to include the confirmation code 63 to confirm that permission of the User 30 was obtained, and the confirmation code 63 sent from the User 30 may involve a viewing by the User 30 of the personal information 12 and a confirmation that it is correct, or that any necessary corrections have been made. The transmission 2113 of FIG. 6B transmits the user ID 17 and the device ID 11 from the certificate authority CA 51 to the backup center 40. The backup center 40 checks that the user ID 17 and the device ID 11 are a valid set that were delivered from the certificate authority 51 as the result of the User 30 confirmation, and upon normal operation, the backup center 40 deactivates the old device ID 11, activates the new device ID 11, updates any coded information 14 associated with the thus identified account (one of 41, 42, etc.), and removes the reservation condition of the account.

FIG. 7 is a flow chart explaining the user authentication process performed by the secure device 10 at the time of log-on by the user.

STEP 140 starts the log-on procedure of STATE-04, of FIG. 2, for the state machine 18 of FIG. 1.

STEP 141 is a conditional judgment that determines whether to backup personal information 12, for example from an information kiosk or from some other device or terminal 20. The decision may be based on a user input, on a set time having elapsed since last backup, or as a last procedure, or if an event has occurred that requires backup, such as, for example. As an example, a user at a computer terminal may have a file, word processor or drawing, that they want to backup at a secure location remote from their personal computer primary storage, or the user may be working at an internet cafe personal computer and wants to store their work at a location where it may be reached when they return to their personal computer, or their laptop or personal computer does not have enough storage for a large file such as a graphics or movie file. If backup is to be performed, processing proceeds to STEP 150.

Figure 8:
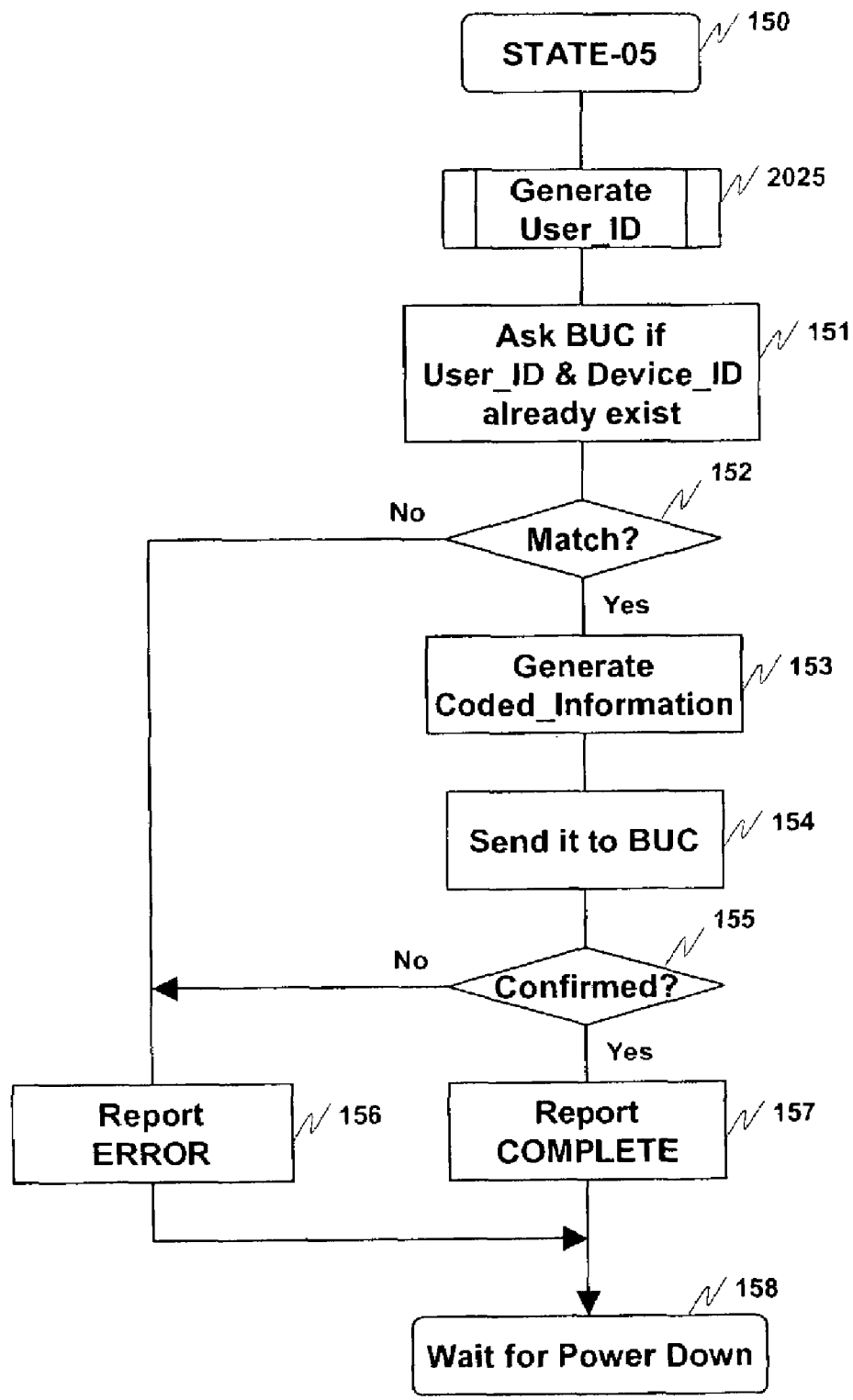
FIG. 8 is a flow chart of the processing of STATE-05, of FIG. 2, for backup of the user's personal information at the backup center.

STEP 150 moves processing to STATE-05, for the backup processing as shown by FIG. 2, which backup process is further illustrated with respect to the flow chart of FIG. 8.

STEP 2014 is reached when the decision process of STEP 141 determines that backup is not being performed. The secure device 10 reads the user PIN 15 of the user 30, for example by receiving an input directly from the user. According to the example, the secure device 10 prompts the user for input of the user PIN 15, for example with a display sent to the screen of the terminal 20, and then waits for the user input.

STEP 142 is a decisional step as to whether or not to cancel, based upon whether or not the user entered a cancel command in response to the prompting provided by step 2014.

STEP 100 is reached when the decision of STEP 142 is a yes and canceling should occur, and then the state machine returns to STATE-00 of FIGS. 2 and 3.

STEP 143 is reached when there is a valid input of PIN 15 from the User 30 as determined by the decision STEP 142. The secure device 10 compares the input from the User 30 with the user PIN 15 that was stored in a nonpublic or inaccessible portion of the memory of the user secure device 10, which was stored during a first use process of STATE 02 or STATE 03.

The group of steps 1400 performs a function of validating the user input, confirmation of data and handling the case where the user input is in error or false.

If decisional STEP 144 determines that the user input of user PIN 15 matches the retrieved PIN 15, then processing continues to STEP 145, of the group of steps 1400. If the decisional STEP 144 returns a negative decision, processing proceeds to STEP 146, of the group of steps 1400.

STEP 145 returns the #1-fail-counter of the user secure device 10 to its initial value.

STEP 212 is a confirmation process, which may be performed by a third party, such as a certification authority CA 50 of FIG. 5B or certification authority CA 51 of FIG. 6B, for approval. The confirmation process is performed by the user 30 reentering PIN 15 or confirming a display of the previously entered PIN 15. Although not necessary, it is preferred and advantageous if the STEP 212 confirms the user PIN 15 value with a value obtained from the backup center 40 and also confirms whether the device ID 11 received from storage within the secure device 10 is the same device ID 11 number as obtained from the backup center 40 for a single account 41, 42, 43, etc of FIG. 1.

STEP 147 is a decisional process dependent upon the result of the confirmation of step 212, to control the branching of further processing.

Figure 9:
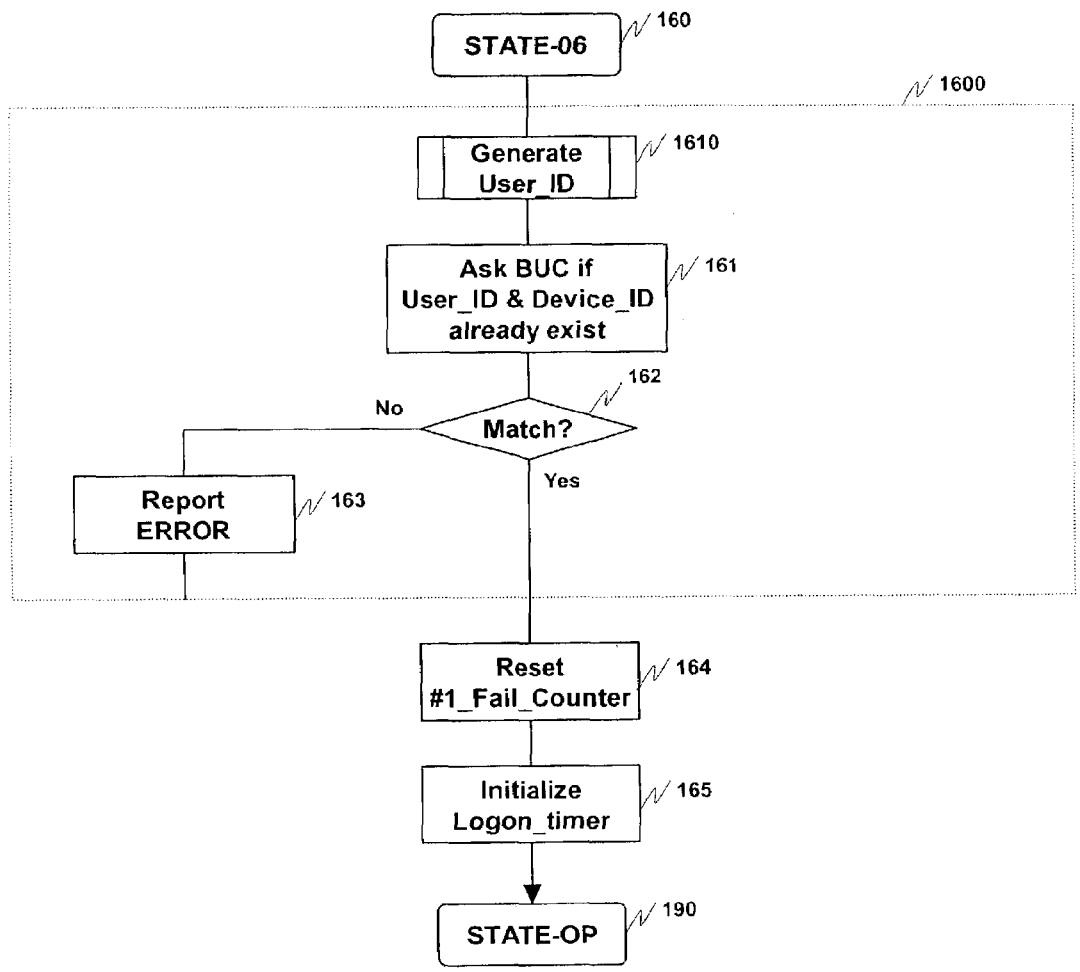
FIG. 9 is a flow chart of the processing of STATE-06 of FIG. 2, for initialization.

STEP 160 is reached when the confirmation process of STEP 212 produced a confirmation as determined by the decisional process 147, and the state machine 18, of FIG. 1, then moves to STATE-06, of FIG. 2 and FIG. 9.

STEP 149 is reached when the decisional process of STEP 147 determines that the confirmation process of STEP 212 has either not produced a confirmation. Because there has been no confirmation, the secure device 10 is disabled and the processing proceeds to the HALT state of STEP 199, which HALT STATE, step 199 is shown in FIG. 2, for the state machine 18.

STEP 146 is reached when the decisional process of STEP 144 returns a negative result. The secure device 10 then increments #1-fail-counter, which is the counter that continuously counts input mistakes.

STEP 148 determines whether the value of the increment #1-fail-counter has reached a preset maximum value. If it has, processing proceeds to step 149. If it has not reached the maximum value, processing proceeds to processing step 140, by entering the state machine into STATE-04, as shown in FIG. 2, which will repeat the processing of the flowchart of FIG. 7.

STEP 149 is reached when the #1-fail-counter has reached the maximum value as determined by decisional step 148. STEP 149, as previously mentioned, disables the secure device 10 and then processing proceeds to the HALT STATE, step 199, of FIG. 2. Once the secure device 10 has entered the HALT STATE, step 199, as set forth in FIG. 7, the secure device 10 remains in the HALT STATE.

STEP 140 of the group of steps 1400 is effectively a return to repeat the entire processing of FIG. 7, and the user is urged to reenter a valid PIN number for a repetition of the above steps.

Figure 11:
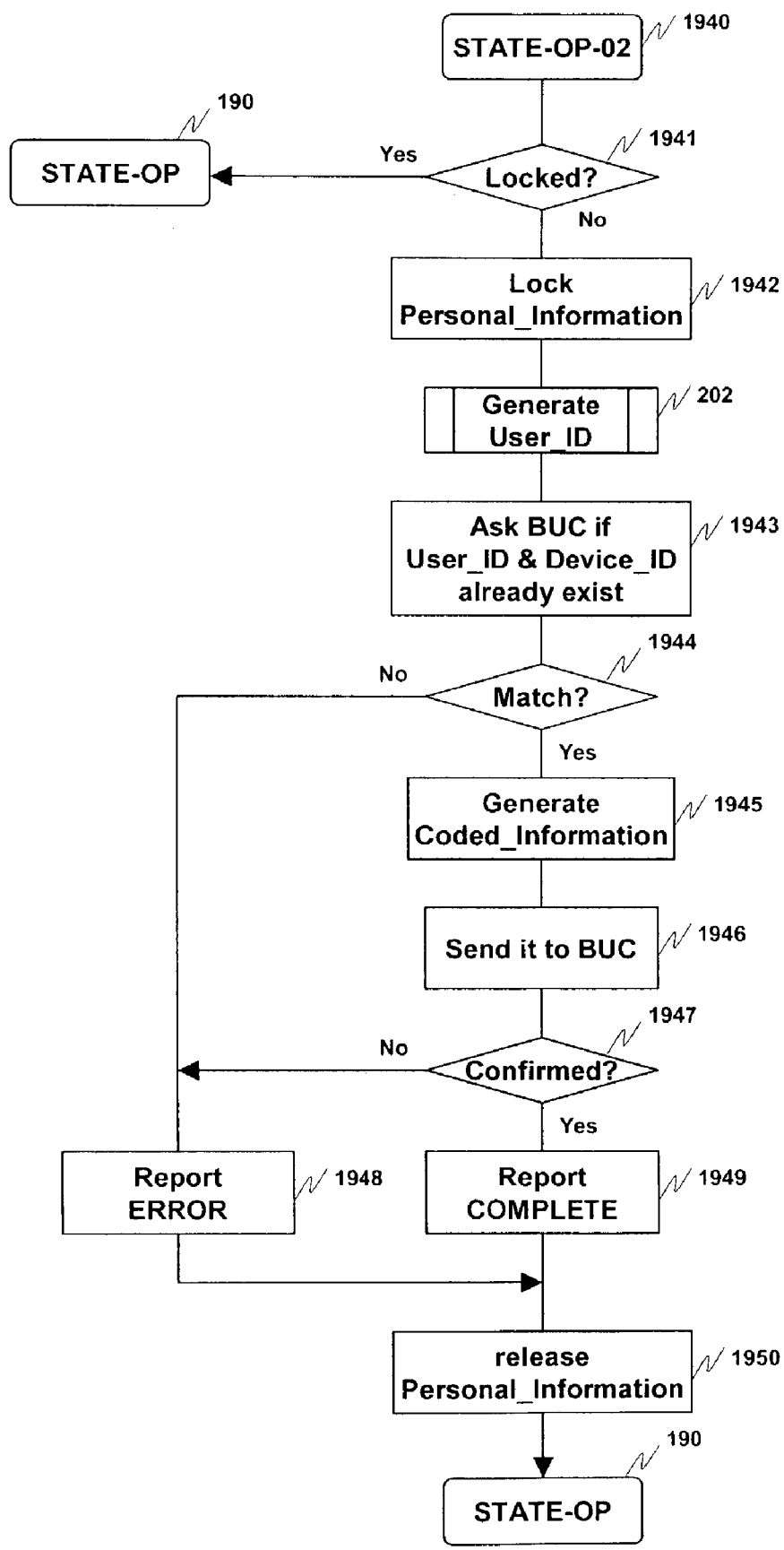
FIG. 11 is a flow chart of the processing of another process of STATE-00, of FIG. 2, for storing coded information at the backup center BUC of FIG. 1.

FIG. 8 is a flow chart for STATE-05, step 150, of FIG. 2, for the backup of coded information 14, shown in FIG. 1, as carried out by the state machine 18 of the Secure Device 10, which is shown in FIG. 1. The backup is to the storage of the backup center BUC 40, after log-on and authentication of the user 30 from STATE-04, of FIG. 2. Similarly, FIG. 11 is a flow chart for STATE OP 02, of the processing carried out by the secure device 10, in backing up the personal information 12 (in the form of encrypted information 14) at the storage of the backup center BUC 40, when a first use processing was performed starting with STATE 01 when a new account is established or an old account is renewed.

STEP 150 starts the backup process of the coded information 14 and is reached after log-on with authentication by the user, according to step 140 of FIG. 2. The secure device 10 performs the processing of STATE-05. The secure device 10 is in communication with the backup center (BUC) 40.

STEP 2025 generates the irreversibly encrypted user ID 17 from the user PIN 15 that was entered by the user 30 during prior STATE 04. The cipher device 13 of FIG. 1 performs the irreversible encryption.

STEP 151 transmits a communication to the backup center BUC 40 and inquires whether the set of irreversibly encrypted user-ID 17 and device ID 11, of FIG. 1, already exist in the storage of the backup center BUC 40 for an account.

STEP 152 is a decisional STEP, where the processing is transferred to STEP 156 if there is no match between the user ID 17 and the device ID 11 with an already registered set of one of the accounts 41, 42, 43 etc of FIG. 1, and processing is transferred to STEP 153, if there is a match.

STEP 156 reports an error to the user 30 when the account identified by the user ID 17 and the device ID 11 does not exist. Then processing proceeds to STEP 158.

STEP 158 includes a wait loop, which waits for power down of the secure device 10 or some command to remove the state machine from the wait loop processing of FIG. 2.

STEP 153 is reached when the decision of STEP 152 is that the backup center database indexing set of encoded user ID 17 and device ID 11 transmitted to the backup center 40 is matched to an existing account, one of accounts 41, 42, 43, etc of FIG. 1. STEP 153 uses the user PIN 15 as an encryption key for encrypting, i.e. coding, the personal information 12 to obtain the encrypted information 14.

STEP 154 transmits the encrypted information 14 to the backup center BUC 40, without transmitting the user PIN 15 to the backup center. Therefore, the encryption key (PIN 15) is not transmitted and cannot be intercepted or otherwise leaked. Further, since the encryption key is not sent to the backup center and the encryption key (PIN 15) cannot be obtained from the irreversibly encrypted user ID 17, the encrypted information 14 is meaningless if intercepted or otherwise leaked.

STEP 155, with a suitable protocol for the exchange of information between the backup center BUC 40 and the user secure device 10, confirms that the backup center BUC 40 has received and successfully stored the encrypted information 14 in association with the correct account as identified by the unique set of database indexing information which in the preferred embodiment is the device ID 11 of the secure device 10 and the irreversibly encrypted user ID 17.

STEP 156 is reached when there is no confirmation, and as previously mentioned, the error is reported to the User 30 and processing proceeds to STEP 158.

STEP 158 includes a wait loop, which waits for power down of the secure device 10 or some command to remove the state machine from the wait loop processing of FIG. 2.

STEP 157 is reached when there is confirmation by the backup center BUC 40 of receipt and proper storage of the encrypted information 14 for the correct account. Therefore, the renewal of personal information 12 or the establishment of the personal information 12 in a newly established account by the backup center BUC 40 is accomplished, as confirmed in step 155 and completion of the coded information backup is reported to the user 30. Thereafter, processing proceeds to STEP 158.

STEP 158 includes a wait loop, which waits for power down of the secure device 10 or some command to remove the state machine from the wait loop processing of FIG. 2.

The backup center BUC 40 receives the coded information 14, user-ID 17 and device-ID 11 from the secure device 10 and attempts to associate the user-ID 17 and device-ID 11 with one of the sets of indexing information of user-ID 17 and device-ID 11 stored at the backup center BUC 40. The stored indexing information combination of secure device ID 17, device ID 11 and the coded information 14 is together a record of one of the accounts 41, 42, etc, of the backup center shown in FIG. 1. When there is a match of user ID 17 and no match of device ID 11 after reviewing the accounts in storage at the backup center, for example, the backup 40 reports that there is no match to secure device 10. The secure device 10 receives the report as the match decision and the backup center refuses the modification of any coded information 14 that is associated with the matched user ID 17. When there is no match of user ID 17 and a match of device ID 11 after reviewing the accounts in storage at the backup center BUC 40, for example, the backup center BUC 40 reports to the user secure device 10 that there is no match. The secure device 10 receives the report as the match decision; and, the backup center refuses the modification of any coded information 14 that is associated with the matched user ID 17. Thus, the backup center 40 uses the user-ID 17 and device-ID 11 for indexing the coded information 14 in storage and retrieval.

In the case where there is no match, the secure device 10 does exception processing to show to the user of the secure device 10 that the secure device 10 was lost in the past, or the like. Also, the secure device 10 does exception processing, because there is the possibility that the secure device 10 is under attack from some other device that has a device ID 11 not registered in the backup center 40. The exception processing may include, as performed by the secure device 10, the personal computer running a program, or the backup center, or a combination of the above, or a third party, a warning is sent by e-mail to the user 30, a message is sent to the secure device 10, the backup center BUC 40, the user or an authority, such as the certification authority 50 or 51, to include information about the illegal or attacking information terminal ID. The information would be used to track the halted device or attacking device at a later time. A halting of communication with the secure device 10 follows the warning, Next, consider the case where the User 30 looses the secure device 10, through theft or an accident, for example, and the User 30 has procured and is now attempting to renew with a new secure device 10, according to STATE 03 of FIG. 2. At the time, the new secure device 10 is in a condition corresponding to that at the time of factory forwarding. Therefore the new secure device 10 has a device ID 11 unique to it and which does not correspond to the lost old secure device 10, which the backup center has paired with the user ID 17. When the user 30 fixes the new secure device 10 to an information terminal 20 of FIG. 1, such as a PC or PDA, the new secure device 10 will inquire of the user whether this operation is that of a new registration or a renewal, STATE 01 of FIG. 2, with the inquiry being made through the information terminal 20. As an alternative embodiment, the application program on the information terminal 20 may handle the inquiry of the user 30 as to whether the operation is one of a new registration or renewal, or the inquiry could be initiated through the backup center BUC 40. In any event, the new secure device 10 communicates such inquiry to the user.

The User 30, in response to the above inquiry of STATE 01, FIG. 2, may reply that the current operation is one of renewal of a new secure device 10 to reach STATE 03, and the secure device 10 and backup center BUC 40 or application program receives the information that the present operation is one of renewal.

The User 30, in response to the above inquiry of STATE-01, FIG. 2, may reply that the current operation is one of opening a new account 41, 42, 43, etc., to reach STATE 02, and the secure device 10 and backup center BUC 40 or application program receives the information that the present operation is one of establishing a new account at the backup center 40.

After either STATE 02 for the opening of a new account at the backup center BUC 40, disclosed in FIG. 5A and FIG. 4B or STATE 03 for the renewal of an existing account at the backup center BUC 40, disclosed in FIG. 6A and FIG. 6B, processing of the state machine 18 of the user secure device 10 of FIG. 1 reaches the condition of STATE 06 of FIG. 2 for initialization, as shown in FIG. 9.

FIG. 9 is a flowchart of STATE 06 of the state machine 18 of FIG. 1. STATE 06 is an initialization procedure that occurs after a first use process, which is the renewal of an old account in FIG. 6A or the establishing of a new account in FIG. 5A or after a successful logon and authentication of STATE 04 shown in FIG. 7. The group of steps 1600 is performed by the state machine 18 in communication with the backup center BUC 40 and cannot be interrupted. The steps 1600 check with the backup center BUC to make sure that the renewal of STATE 03 or the new account establishment of STATE 02, each of which changed or modified the indexing information of the device ID 11 and user ID 17 at the backup center, was performed accurately at the backup center BUC 40.

STEP 160 starts the processing of STATE 06, following either STATE 02 or STATE 03.

STEP 1610 generates the unique encrypted user ID 17 by irreversible conversion from the user PIN 15, by using the ID generator 16 of FIG. 1 for the secure device 10. The value of the user PIN 15 is obtained from the secure storage within the secure device 10.

STEP 161 queries the database of the backup center, BUC 40 shown in FIG. 1, to determine if the User ID 17 and the device ID 11 already exist in one of the accounts 41, 42, 43, etc.

STEP 162 determines if the device ID 11 and generated user ID 17 match a pair of corresponding information for a single account 41, 42, 43, etc, which decision is based upon a response from the backup center BUC 40.

STEP 163 is reached when there is no match in step 162. The error is reported, for example, to one or both of the user 30 and certification authority CA 50 or 51.

STEP 164 is reached when there is a match in step 162. The reset #1 fail counter of steps 145 and 146 of FIG. 7 is reset.

STEP 165 initializes the logon timer, which is used in steps 2012 of FIG. 5A, 2013 of FIG. 6A and 2014 of FIG. 7. The logon timer times out if the user 30 does not enter a requested PIN 15 within a maximum allowed time.

STEP 190 is the STATE-OP of the state machine 18 of FIGS. 1 and 2, performed, for example, as either STATE-OP-01 or STATE-OP-02.

FIGS. 10A, 10B and 10B show a single flowchart for STATE OP 01, which is one of the operations of STATE OP, process 190, of FIG. 2, as performed by the state machine 18 of the secure device shown in FIG. 1.

STEP 201 reads the user PIN 15 as a process input, comes from the user 30 after inquiry, which input is therefore the user PIN 15 or a cancel command. The user PIN 15 may be defined by the aggregation of a plurality of authentication codes, for example a user name (PIN) and user password (PIN), STEP 1911 performs a decision as to whether or not to cancel the process. If the User 30 inputs a cancel command, processing proceeds to STATE OP, which is operation 190 of FIG. 2, for the state machine 18.

STEP 190 is STATE OP of the state machine 18 of FIG. 1 and 2, performed either as STATE OP 01 or STATE OP 02.

STEP 1912 is reached when there is a valid input of PIN 15 as determined by the decision STEP 1911. The secure device 10 compares the input with a securely stored user PIN 15.

STEP 1913 determines if there is a match result of the comparison performed in step 1912.

STEP 1914 is reached when the decisional process of STEP 1913 returns a negative result from comparing the PIN 15 stored within the secure device 10 and the PIN 15 entered by the user 30 in step 201. The secure device 10 then increments #1-fail-counter, which is the counter that continuously counts input mistakes.

STEP 1915 determines whether the value of the increment #1-fail-counter has reached a preset maximum value. If it has, processing proceeds to step 1910. If it has not reached the maximum value, processing proceeds to processing step 1916.

STEP 1910 passes the processing to STATE-OP-01, which returns to the top of the flowchart of FIG. 10-A STEP 1916 is reached when the decisional process of STEP 1913 determines that the confirmation process of STEP 1912 has not produced a confirmation of the user PIN 15 and the counter of step 1914 has exceeded the maximum value of step 1915. Because there has been no confirmation, the secure device 10 is disabled. Thereafter, processing proceeding to the HALT state of STEP 199.

STEP 199 is the STATE-HALT condition in FIG. 2 of the state machine 18, which nullifies the secure device 10 so that it has no further function.

STEP 1917 returns the #1-fail-counter to its initial value.

STEP 202 generates the encrypted user ID 17 from the PIN 15 by irreversible encryption.

STEP 1918 transmits a communication to the BUC (backup device) 40 and inquires whether the set of irreversibly encrypted user ID 17 and device ID 11 already exist in the storage of the backup center 40 for an account 41, 42, 43, etc of FIG. 1.

STEP 1919 is a decisional step, where the processing is transferred to STEP 1920 if there is no match between the user ID 17 and the device ID 11 as reported by the backup center BUC 40, with respect to an already registered set for one of the accounts 41, 42, 43 etc of FIG. 1. Processing is transferred to STEP 1921, if there is a match.

STEP 1920 is a process that is performed by the secure device 10. The secure device 10 reports an error if an account, identified by the user ID 17 and the device ID 11, does not exist at the backup center BUC 40. Then processing proceeds to step 190, which transfers further processing to the STATE OP of the state machine as shown in FIGS. 1 and 2.

STEP 190 is STATE-OP of the state machine 18 of FIGS. 1 and 2, performed either as STATE OP 01 or STATE OP 02.

STEP 1921 indicates the process flows from FIG. 10A to FIG. 10B by the connection OP011, which is labeled 1921, although it is not really a step.

STEP 1922 requests the user to enter a new user PIN 15, because the previously entered PIN 15 of this user 30 in trying to set up a first use from STATE-00 was found to already exist in another account or not to exist at the backup center with the device ID 11.

STEP 201 reads the user 30 input, which may be the requested user PIN 15 or a cancel command. The user PIN 15 may be defined by the aggregation of a plurality of authentication codes, for example a user name (PIN) and user password (PIN), STEP 1923 performs a decision as to whether or not to cancel a renewal process. If the User 30 inputs a cancel command, processing proceeds to STATE OP, which is operation 190 of FIG. 2, for the state machine 18.

STEP 190 is STATE OP of the state machine 18 of FIGS. 1 and 2, performed either as STATE-OP-01 or STATE-OP-02.

STEP 1924 requests the user to reenter their user PIN 15, as the start of a confirmation.

STEP 201 reads the user PIN 15 entered in step 1922. The user PIN 15 may be defined by the aggregation of a plurality of authentication codes, for example a user name (PIN) and user password (PIN), STEP 1925 performs a decision as to whether or not to cancel, for example the renewal process. If the User 30 inputs a cancel command, processing proceeds to STATE OP, which is operation 190 of FIG. 2, for the state machine 18.

STEP 190 is STATE OP of the state machine 18 of FIGS. 1 and 2, performed either as STATE OP 01 or STATE OP 02.

STEP 1926 is reached when the user has not cancelled as determined by step 1925. If there is confirmation, that is if the re-entry of step 1924 matches the entry of a new user PIN 15 in step 1922, processing proceeds to Figure C, through step 1927. If there is no match as determined by the decision of step 1926, the confirmation fails and processing returns to step 1922.

STEP 1927 indicates the process flow from FIG. 10B to FIG. 10C is shown by the connection OP012, which is labeled 1927, although it is not really a step.

STEP 202 generates the encrypted user ID 17 from the PIN 15 by irreversible encryption.

STEP 321 inquires of the backup center BUC 40 whether or not the encrypted user ID17 is already registered at the backup center 40.

STEP 1928 decides if the user ID 17 generated in step 202 is unique in the backup center storage, depending upon the response of the backup center BUC 40 to the inquiry or step 321.

STEP 1929 requests the user 30 to change the PIN 15, for example through the display or audio capability of the computer 20, STEP 1921 indicates the process flow from FIG. 10C to FIG. 10A is shown by the connection OP011, which is labeled 1921, although it is not really a step.

STEP 1930 temporarily pre-registers the new user PIN 15 in the secure storage of the secure device 10.

STEP 322 requests that the backup center 40 register the encrypted user PIN 17 and the device ID 11 as the indexing information of a new account.

STEP 1931 decides if the registry of the new encrypted user PIN 17 at the backup center 40 was confirmed by the backup center 40 in response to the request of step 322.

STEP 1934 deletes the user PIN that was pre-registered in step 1930.

STEP 1935 reports an error to the user 30 when there is no confirmation. Then processing proceeds to STEP 190. The report may be communicated in any manner, for example by use of the normal monitor screen of the computer 20 of FIG. 1, or by email to the user, for example.

STEP 190 is STATE OP of the state machine 18 of FIGS. 1 and 2, performed either as STATE OP 01 or STATE OP 02.

STEP 1932 registers the new user PIN, which may be registered in the secure storage of the secure device 10 as user PIN 15 or in the form of encrypted user ID 17

STEP 1933 reports to the user 30 that the changing of the user PIN processing has been satisfactorily completed. The report may be communicated in any manner, for example by use of the normal monitor screen of the computer 20 of FIG. 1 or by sending the user an email, for example.

STEP 190 is STATE OP of the state machine 18 of FIGS. 1 and 2, performed either as STATE OP 01 or STATE OP 02.

The flow chart of FIG. 11 shows the processing of the state machine 18 for STATE OP 02, which is one of the operations of STATE OP, process 190 of FIG. 2.

STATE OP 02 begins with STEP 1940 and is for backing up the personal information 12 at the backup center, BUC, for example after first use processing of STATE 01 and STATE 02 or STATE 03, when a new account is established or renewal of an old account is established.

STEP 1941 determines whether the secure device 10 is locked. If the secure device 10 is locked, processing proceeds to STEP 190, STATE OP of the state machine, a condition where the User 30 has already logged on. By way of an example, one set of sign-on personal information 12 is received by the secure device 10 when the User 30 registers at a new WAN (wide area network), for example the internet and more particularly the WWW (world-wide web), site 90. The sign-on information 12 may be the user name, password, URL addresses of web sites of interest, e-mail address, and the like that would be needed to log-on to different web sites. The personal information 12 does not leak at this time due to the cipher communication, such as SSL, between the secure device 10 and the corresponding site of the exchange.

The locked decision of STEP 1941 judges whether the personal information 12 is received during processing with a renewal. If the processing is one with a renewal, the decision STEP 1941 passes to the processing STEP 190 to stop the backup and return to the STATE OP, step 190.

When the secure device 10 receives new personal information, after first use processing of STATE 01 and STATE 02 or STATE 03, the secure device 10 commands the backup of the new personal information 12 to the BUC (backup center) 40, particularly when the sign-on information such as the personal information 12 is newly registered in the secure device 10. The backup preferable occurs automatically according to the judgment of the secure device 10, or when the User 30 specifically indicates an explicit target.

STEP 1942 is reached when the state machine determines that the secure device 10 is not locked in accordance with the decision STEP 1941. STEP 1941 and STEP 1942 are indivisible, in that state machine 10 will not accept interruption in the handling between these steps, that is, the processing from STEP 1941 to STEP 1942 cannot be interrupted, according to the preferred embodiment. This is an exclusive control technique that is known as semaphore processing.

The renewal of personal information 12 will be inhibited by the inseparable processing of STEP 1942, if the renewal is not during processing. The inhibition of renewal continues until it is released with STEP 1950, as will be explained.

STEP 202 is reached after the performance of STEP 1942, and the secure device 10 generates the encrypted user ID 17 from the PIN 15 by irreversible encryption.

STEP 1943 transmits a communication to the BUC (backup device) 40 and inquires whether the set of user-ID 17 and device ID 11 already exist in the storage of the backup center 40.

STEP 1944 is a decisional step, where the processing is transferred to STEP 1948 if there is no match between the user ID 17 and the device ID 11 with respect to an already registered corresponding set for one of the accounts 41, 42, 43 etc of FIG. 1. Processing is transferred to STEP 1945 when there is a match. STEP 1948 is performed by the secure device in reporting an error if the account, identified by the user ID 17 and the device ID 11, does not exist. The error may be reported to the user 30 through the display of the personal computer 20 or by email. Then processing proceeds to STEP 1950.

STEP 1950 prevents renewal of personal information 12 by releasing the personal information 12 and then returns to the STATE OP, STEP 190, of FIG. 2.

STEP 1945 is reached when the decision of STEP 1944 is that the personal information set of encoded user ID 17 and device ID 11 transmitted to the backup center is matched to an existing account at the backup center BUC 40, that is one of the accounts 41, 42, 43, etc of FIG. 1. STEP 1945 uses the user PIN 15 as an encryption key for encrypting or coding the encrypted information 14 from the personal information 12.

STEP 1946 transmits the now encrypted information 14 to the backup center 40, without transmitting the user PIN 15 to the backup center. Therefore, the encryption key of PIN 15 is not transmitted and cannot be intercepted. Further, since the encryption key PIN 15 is not sent to the backup center, the encrypted information 14 at the backup center is meaningless, and the encryption key, i.e., PIN 15, cannot be obtained from the user ID 17, because user ID 17 is irreversibly encrypted.

STEP 1947, with a suitable protocol for the exchange of information, confirms that the backup center has received and successfully stored the encrypted information 14 in association with the correct account as identified by the unique set of information, which in the preferred embodiment is the device ID 11 of the secure device 10 and the irreversibly encrypted user ID 17.

STEP 1948 is reached when there is no confirmation in step 1947. As previously mentioned, the error is reported to the User 30 and processing proceeds to STEP 1950.

STEP 1950 prevents renewal of personal information 12 by releasing the personal information 12 and then returns to the STATE OP, STEP 190, of FIG. 2.

STEP 1949 is reached when there is confirmation by the backup center of receipt and proper storage of the encrypted information 14 for the correct account, as determined in step 1947. The completion of the backup of the coded information 14 at the backup BUC 40 is reported to the user 30 and processing proceeds to STEP 1950.

STEP 1950 prevents renewal of personal information 12 by releasing the personal information 12. Therefore, the renewal of personal information 12 is permitted after the completion of the backup is reported to the user in STEP 1949. Thereafter, the state machine returns to STATE OP, in STEP 190, of FIG. 2.

The secure device 10 may be a card, particularly a memory card such as a smart card. The secure device is preferably a small inexpensive device, which may be purchased at one of a plurality of retail outlets.

With respect to the various entries made by the User 30, there may be a time-out period, which will cancel the processing if the user takes too much time in providing the requested information. Also, there is an error counter wherein the User 30 has a fixed maximum number of attempts within which to provide some confirmation or valid requested information, and upon exceeding the number of attempts, the system will shut down and go into an error mode. Further, if the reservation condition of an account is not removed within a fixed time period, the account is removed or otherwise deactivated.

The secure device 10 preferably stores the user PIN 15 permanently in an area not accessible from the outside and which storage area is a tamper-proof memory well known at the present time. Alternatively, as mentioned, the PIN 15 may be only temporarily stored for the specific process step being performed and thereafter it is erased, requiring reentry of the PIN 15 if it is later needed. As an alternative to temporary storage or permanent inaccessible storage of the user PIN 15 on the secure device 10, the user PIN 15 may be stored permanently in the secure device 10 and then automatically erased when the secure device 10 is powered down.

According to the broader aspects of the present invention, which relate to storage and backup storage security in general, the backup center storage can be a hard disc of a personal computer, backing up some other permanent storage at a remote location, or permanent storage at the computer or at a remote site backing up the volatile or temporary storage of the computer. For example the backup may be at a central internet site that is accessible as a general purpose storage area for the public, storage such as a flash memory or a chip memory card such as a smart card, the storage of a PDA that would preferably have user interface software, or merely be a storage place for documents, with the documents being encrypted and secured in storage according to the invention.

The secure device 10 has a field flag that is set by an outside billing agency to automatically cancel or at least temporarily disable the secure device 10 if the user 30 has not made suitable payments for its use, which is another example of the secure device 10 being lost, in the sense of being lost to further use by the user 30, that is, lost for the use by the User 30 at least until the billing account is made current by a payment from the User 30. The field 411, 421, 431, etc, for the individual accounts 41, 42, 43, etc of FIG. 1 may be used to contain accounting information, for example a flag indicating an up to date payment on the account has been made.

Some examples of communication have been set forth generally, with respect to the communication between the user 30, user secure device 10, agent, certification authority CA and backup center BUC. The communication methods actually employed may be of various kinds commonly used in the communication or transmission of data. The secure device 10 and the backup center 40 may communication with each other by IPSec, SSL or other cipher communication protocols. In such cases, the secure device 10 executes the protocol processing function, such as IPSec, SSL, or other cipher communication protocols, inside the secure device 10, by protocol processing that is not shown in detail because it may be conventional. Because of this, any program running on the information terminal 20 is unable to know the communication contents, even though those communications are performed through the information terminal 20. In a similar manner, any apparatus in an intermediate position in the communication path between the information terminal 20 and the backup center 40 is unable to know the communication contents, because the cipher data comes and goes until it reaches the server inside the backup center 40. Therefore, the user's secure device 10 may be coupled to an information terminal 20 in an Internet Café, for example, without compromising the security of transmitted data.

Accordingly, the present invention is generally used for secure storage of computer readable information or data.

Computer readable media to carry code for implementing the embodiments refers to any medium that participates in providing according to the invention to a processor for execution. Examples include non-volatile media or volatile media. Non-volatile media includes, for example: optical or magnetic flexible discs or tapes and hard disks, and more specifically CD-ROM, CDRW and DVD; and punch cards, paper tape, optical mark sheets or any other physical medium with patterns of holes. In general computer readable media as used herein includes any physical fixation, temporary or more permanent, from which a computer can read code.

Transmission couplings between the secure device 10 and the computer 20 or the secure device as the un-illustrated PDA or laptop computer or other portable device include coaxial cables, copper wire, wireless links and fiber optics, which may send acoustic, optical or electromagnetic waves, such as those generated during radio frequency (RF) and infrared (IR) data communications.

For security reasons and when the personal information 12 includes information to provide access to the site, such personal information 12 may be changed periodically and automatically or changed at any time at the option of the user. In that case, the personal information 12 is coded by the user PIN, and the encoded information 14 is stored to the backup center periodically or optionally. If the secure device 10 is used, it may not be necessary to change the personal information 12. Therefore, if such personal information 12 is changed automatically of manually, the changed information is stored to the backup center.

While the present invention has been described in connection with a number of embodiments, implementations, modifications and variations that have advantages specific to them, the present invention is not necessarily so limited, but covers various obvious modifications and equivalent arrangements according to the broader aspects, all according to the spirit and scope of the following claims.

What is claimed is:

1. A portable secure device for an information processing terminal, comprising:
   a data transmission coupling for controlling access to the information processing terminal by a user, the portable secure device being capable of connecting and disconnecting with the information processing terminal via the data transmission coupling;
   a computer readable storage medium having thereon computer readable data executable to control sending and obtaining data through said data transmission coupling to and from a separate data storage;
   said medium having thereon computer readable data representing a unique portable secure device ID;
   said medium having thereon computer readable data executable to control irreversibly encrypting a unique user PIN to obtain a unique irreversibly encrypted user ID;
   said medium having thereon computer readable data executable to control sending the unique portable secure device ID and the unique irreversibly encrypted user ID to the separate data storage to establish a record indexed on a combination of the unique portable secure device ID and the unique irreversibly encrypted user ID;
   said medium having thereon computer readable data executable to control reversibly encrypting user information to obtain reversibly encrypted user information; and,
   said medium having thereon computer readable data executable to control sending the reversibly encrypted user information, the unique portable secure device ID, the unique irreversibly encrypted user ID and a request for storage to the separate data storage to become part of the record indexed on the combination of the unique portable secure device ID and the unique irreversibly encrypted user ID.

2. The portable secure device of claim 1, further comprising:
   said medium having thereon computer readable data executable to control the reversibly encrypting of the information with an encryption key that is different from the irreversibly encrypted user ID.

3. The portable secure device of claim 1, further comprising:
   said medium having thereon computer readable data executable to control the reversible encrypting of the information with an encryption key that is the unique user PIN or a derivative thereof.

4. The portable secure device of claim 1, further comprising:
   said medium having thereon computer readable data executable to control sending, to the separate data storage, the unique irreversibly encrypted user ID together with a request for establishment of a new storage account for the user; and
   said medium having thereon computer readable data executable, in response to receiving a notification that the irreversibly encrypted authentication code already exists at the separate data storage, to prompt the user for entry of a different unique user PIN.

5. The portable secure device of claim 1, further comprising:
   said medium having thereon computer readable data executable to control sending, to the separate data storage, the unique irreversibly encrypted user ID, a new unique device ID and a request for renewal of a storage account with the new unique device ID and deactivation of the previous unique device ID.

6. The portable secure device of claim 1, further comprising:

said medium having thereon computer readable data executable to control sending, to the separate data storage, the unique irreversibly encrypted user ID, the unique secure device ID and a request for stored information corresponding only to both the irreversibly encrypted user ID, the unique secure device ID.

7. A method for authentication vicarious execution, performed by the portable secure device of claim 1, comprising the steps of:

receiving input of a user PIN;

irreversibly encrypting the user PIN to obtain the irreversibly encrypted user ID;

receiving personal information from the user;

encrypting the personal information with the user PIN as an encryption key to obtain the reversibly encrypted information;

sending the unique irreversibly encrypted user ID, the reversibly encrypted information, and the unique device ID along with a request for storage of the encrypted information to the separate data storage for backup of the encrypted information without disclosing the user's identity and the user PIN to the BUC; and automatically providing personal information with WAN sites visited by the user as needed or requested by the sites to function as the user's agent without using the separate data storage.

8. The method of claim 7, wherein said sending includes sending a destination for the request that is a WAN site remote from the portable secure device.

* * * * *